(12) United States Patent
Liang et al.

(10) Patent No.: US 11,835,707 B2
(45) Date of Patent: Dec. 5, 2023

(54) SCANNING OPTICAL IMAGING DEVICE

(71) Applicant: Massachusetts Institute of Technology, Cambridge, MA (US)

(72) Inventors: Kaicheng Liang, Cambridge, MA (US); James G. Fujimoto, Cambridge, MA (US); Osman Oguz Ahsen, Cambridge, MA (US); Michael Gene Giacomelli, Cambridge, MA (US); Hsiang-Chieh Lee, Cambridge, MA (US); Zhao Wang, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 877 days.

(21) Appl. No.: 16/496,371

(22) PCT Filed: May 3, 2018

(86) PCT No.: PCT/US2018/030925
§ 371 (c)(1),
(2) Date: Sep. 20, 2019

(87) PCT Pub. No.: WO2018/204674
PCT Pub. Date: Nov. 8, 2018

(65) Prior Publication Data
US 2021/0109340 A1    Apr. 15, 2021

Related U.S. Application Data

(60) Provisional application No. 62/501,365, filed on May 4, 2017.

(51) Int. Cl.
*A61B 1/00* (2006.01)
*G02B 23/26* (2006.01)
(Continued)

(52) U.S. Cl.
CPC ........ *G02B 23/26* (2013.01); *A61B 1/00165* (2013.01); *A61B 1/00172* (2013.01);
(Continued)

(58) Field of Classification Search
CPC .................... G06T 2207/10068; G02B 7/001
See application file for complete search history.

(56) References Cited

U.S. PATENT DOCUMENTS

| 3,532,037 A | 10/1970 | Auphan et al. |
| 7,625,335 B2 * | 12/2009 | Deichmann ............ G01B 11/25 600/117 |

(Continued)

FOREIGN PATENT DOCUMENTS

| WO | 2014/113506 A1 | 7/2014 |
| WO | 2015/153982 A1 | 10/2015 |

(Continued)

OTHER PUBLICATIONS

"Notification of Transmittal of The International Preliminary Report on Patentability and The Written Opinion of the International Searching Authority," for International Application No. PCT/US2018/030925, entitled "Scanning Optical Imaging Device" dated Nov. 5, 2019; 11 pages.

(Continued)

*Primary Examiner* — Brian T Pendleton
*Assistant Examiner* — Frank Johnson
(74) *Attorney, Agent, or Firm* — Hamilton, Brook, Smith & Reynolds, P.C.

(57) ABSTRACT

The present disclosure pertains to an apparatus and methods of an imaging device for obtaining images from the walls of luminal organs or a surgical cavity. The device is capable of passage through luminal organs or introduction into surgical cavities, and obtains images by rapidly scanning a focused light beam on the tissue to be imaged and receiving light (Continued)

from the tissue. The device comprises at least one mechanism for projecting a 2-dimensional (2-D) optical pattern, such as a 2-D scanner (508) or a 2-D optical array forming a closed loop scan pattern (506). The device comprises at least one other beam scanning mechanism, such as a rotary or angular scanner (510) such that cycloid scan pattern is formed on the surface to be scanned, and also has embodiments of focusing optics at different regimes of numerical aperture. The disclosure also describes methods for accurate image reconstruction with embodiments of hardware control and post-acquisition processing.

46 Claims, 24 Drawing Sheets

(51) Int. Cl.
  *G02B 26/10* (2006.01)
  *A61B 5/00* (2006.01)
(52) U.S. Cl.
  CPC ........ *A61B 1/00188* (2013.01); *A61B 5/0066* (2013.01); *A61B 5/0068* (2013.01); *G02B 26/103* (2013.01)

(56) References Cited

U.S. PATENT DOCUMENTS

| | | | |
|---|---|---|---|
| 8,928,746 B1 | 1/2015 | Stevrin et al. | |
| 9,173,569 B2 | 11/2015 | Elmaleh et al. | |
| 9,186,067 B2 | 11/2015 | Tearney et al. | |
| 9,439,570 B2 | 9/2016 | Vertikov | |
| 9,513,276 B2 | 12/2016 | Tearney et al. | |
| 9,615,748 B2 | 4/2017 | Tearney et al. | |
| 9,683,928 B2 | 6/2017 | Swanson | |
| 2004/0158159 A1* | 8/2004 | Seto | A61B 1/051 600/476 |
| 2006/0072874 A1* | 4/2006 | Johnston | G02B 23/243 385/25 |
| 2006/0195014 A1* | 8/2006 | Seibel | A61B 1/00172 600/102 |
| 2007/0282197 A1 | 12/2007 | Bill et al. | |
| 2008/0161641 A1 | 7/2008 | Nakazato et al. | |
| 2009/0092364 A1* | 4/2009 | Johnston | A61B 1/00172 385/116 |
| 2009/0316116 A1* | 12/2009 | Melville | G03B 21/00 348/742 |
| 2010/0022858 A1* | 1/2010 | Gono | G01N 21/474 600/310 |
| 2010/0141829 A1* | 6/2010 | Jalali | A61B 5/0062 382/280 |
| 2010/0210937 A1 | 8/2010 | Bouma et al. | |
| 2012/0004506 A1 | 1/2012 | Tearney et al. | |
| 2012/0330102 A1* | 12/2012 | Brennan | A61B 1/00096 600/177 |
| 2013/0027516 A1* | 1/2013 | Hart | A61B 5/0071 348/45 |
| 2013/0158393 A1* | 6/2013 | Papac | A61N 5/062 606/17 |
| 2013/0190565 A1 | 7/2013 | Gora et al. | |
| 2013/0310643 A1* | 11/2013 | Gora | A61B 1/00016 600/109 |
| 2014/0005758 A1 | 1/2014 | Ben-Yehuda et al. | |
| 2014/0187999 A1 | 7/2014 | Tearney et al. | |
| 2014/0232993 A1 | 8/2014 | Kim | |
| 2014/0236022 A1* | 8/2014 | Zeng | A61B 1/0125 600/476 |
| 2015/0377613 A1 | 12/2015 | Small et al. | |
| 2016/0135892 A1* | 5/2016 | Yu | A61B 18/24 606/11 |
| 2016/0227990 A1 | 8/2016 | Li et al. | |
| 2017/0041577 A1 | 2/2017 | Nishimura | |
| 2017/0143196 A1 | 5/2017 | Liang et al. | |
| 2017/0143214 A1 | 5/2017 | Garibotto et al. | |
| 2017/0265879 A1* | 9/2017 | Washburn, II | A61M 25/10 |
| 2017/0280970 A1 | 10/2017 | Sartor et al. | |
| 2017/0366773 A1* | 12/2017 | Kiraly | H04N 5/2256 |
| 2018/0168729 A1* | 6/2018 | Pratten | A61N 1/362 |
| 2018/0364154 A1* | 12/2018 | Wu | A61B 1/00 |
| 2019/0374092 A1* | 12/2019 | Wu | G01J 3/0218 |
| 2020/0096753 A1* | 3/2020 | Oldham | G02B 21/0048 |

FOREIGN PATENT DOCUMENTS

| | | |
|---|---|---|
| WO | 2016/170612 A1 | 10/2016 |
| WO | 2017/059246 A1 | 4/2017 |
| WO | 2018/204674 A1 | 5/2018 |

OTHER PUBLICATIONS

Chen, Shih-Chi, et al., "Thermomechanical Actuator-Based Three-Axis Optical Scanner for High-Speed Two-Photon Endomicroscope Imaging," Journal of Microelectromechanical Systems, 23(3): 570-578 (Jun. 2014).

Veinberg, V.B., et al., "Fiber Endoscopes With Structureless Image," Biomedical Engineering, Consultants Bureau, New York, NY, US, vol. 13, No. 5, pp. 241-246 (Aug. 1979).

Yong, Y.K., et al., "High-speed cycloid-scan atomic force microscopy," Nanotechnology, 21(36): 365503, 4 pages total (Aug. 2010).

International Search Report and Written Opinion for Int'l Application No. PCT/US2018/030925, titled: Scanning Optical Imaging Device, dated Sep. 21, 2018.

Dong, et al., "Tethered Capsule Endomicroscopy: A New Window into the Upper Gastrointestinal Tract," In Nanophotonics, Neurophotonics and Biomedical Spectroscopy, 2019, pp. 503-519, ISBN 9780323480673.

Kim, et al., "Diagnostic Fiber-Based Optical Imaging Catheters," Biomedical Engineering Letters 4, 239-249 (2014).

Seibel, et al., "Tethered Capsule Endoscopy, a Low-Cost and High-Performance Alternative Technology for the Screening of Esophageal Cancer and Barrett's Esophagus," IEEE Trans Biomed Eng. Mar. 2008; 55(3):1032-42.

Gora, et al., "Tethered Capsule Endomicroscopy Enabled Less-Invasive Imaging of Gastrointestinal Tract Microstructure," Nat Med. Feb. 2013; 19(2): 238-240; published online Jan. 13, 2013. doi: 10.1038/nm.3052.

\* cited by examiner

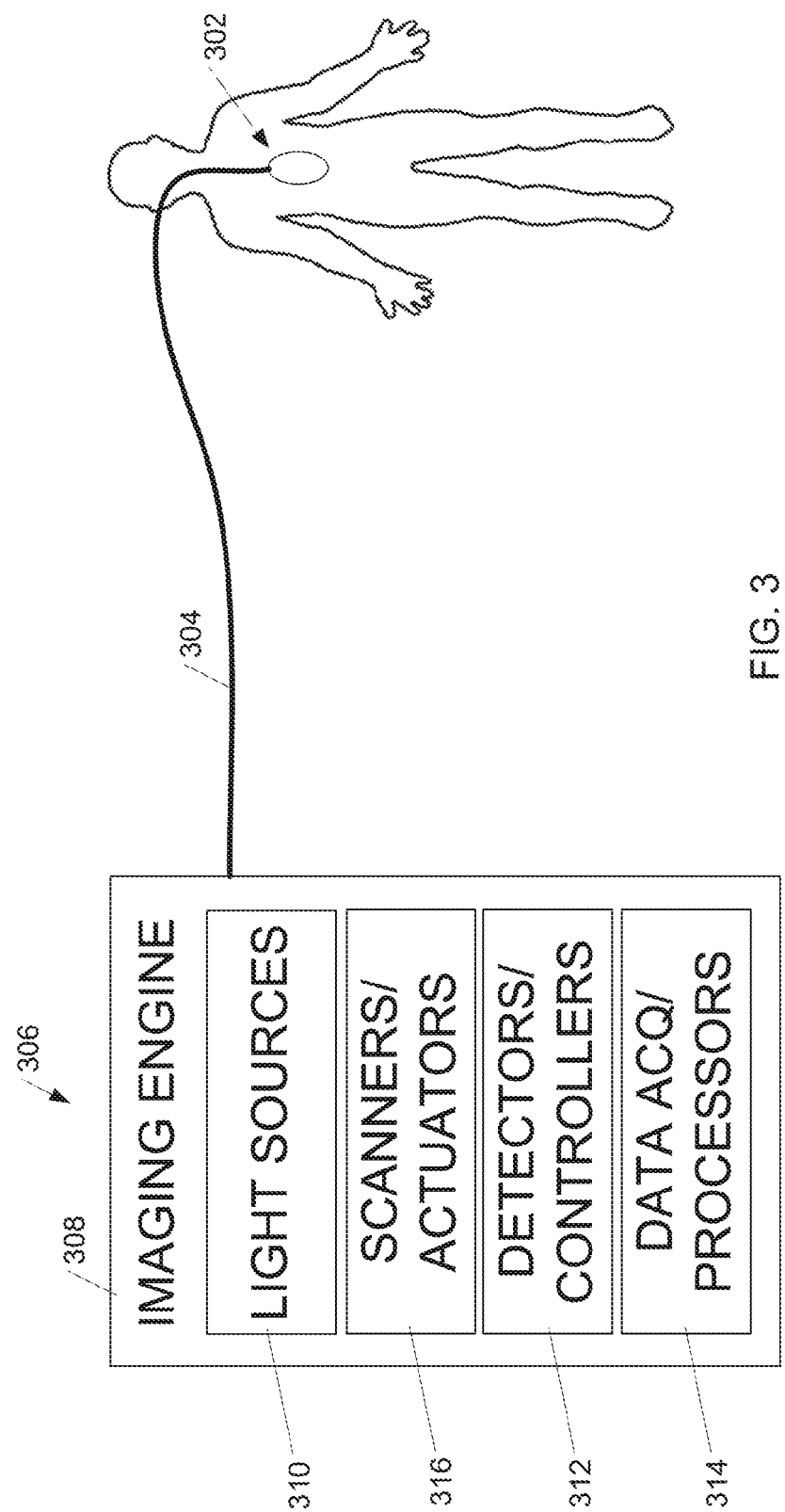

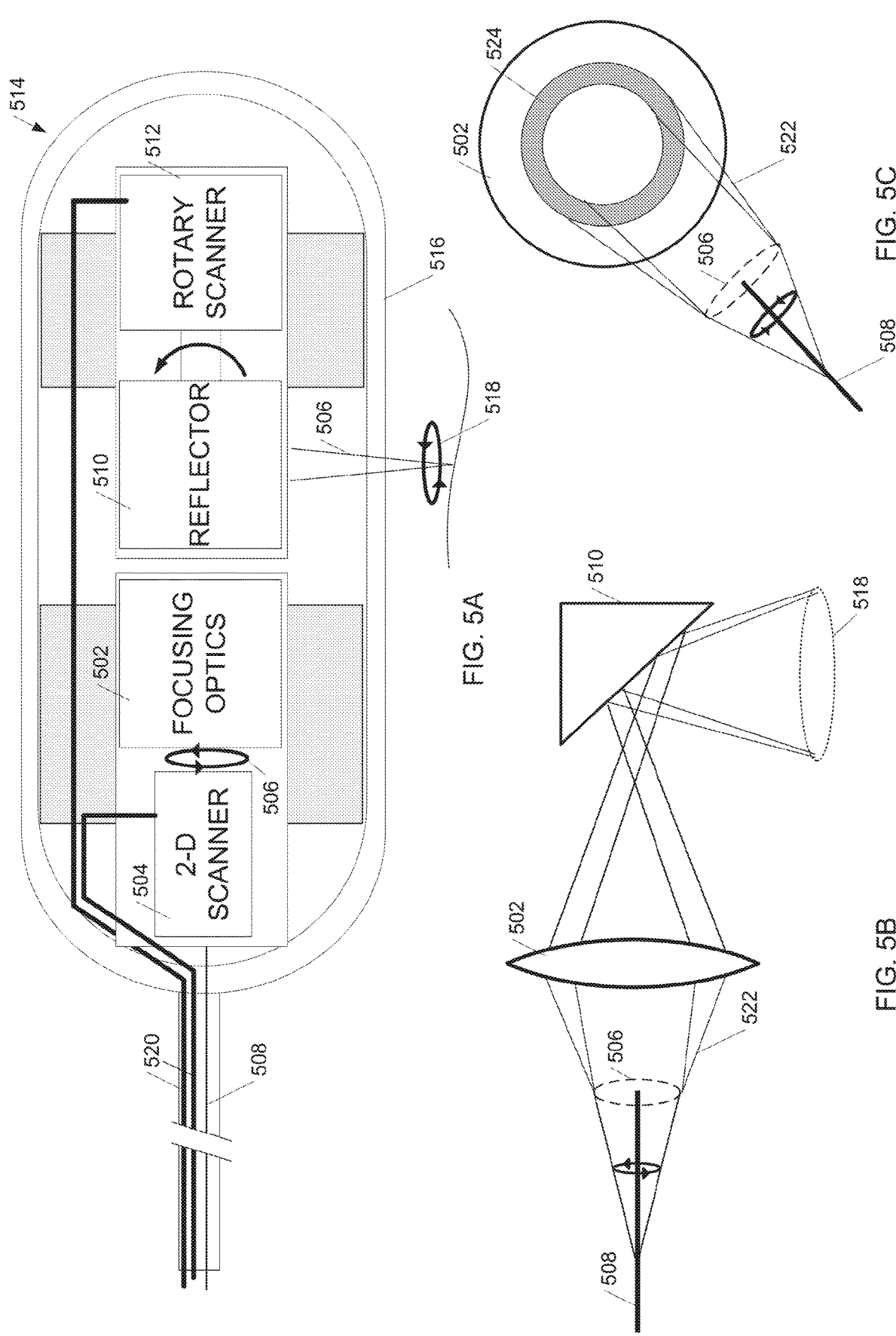

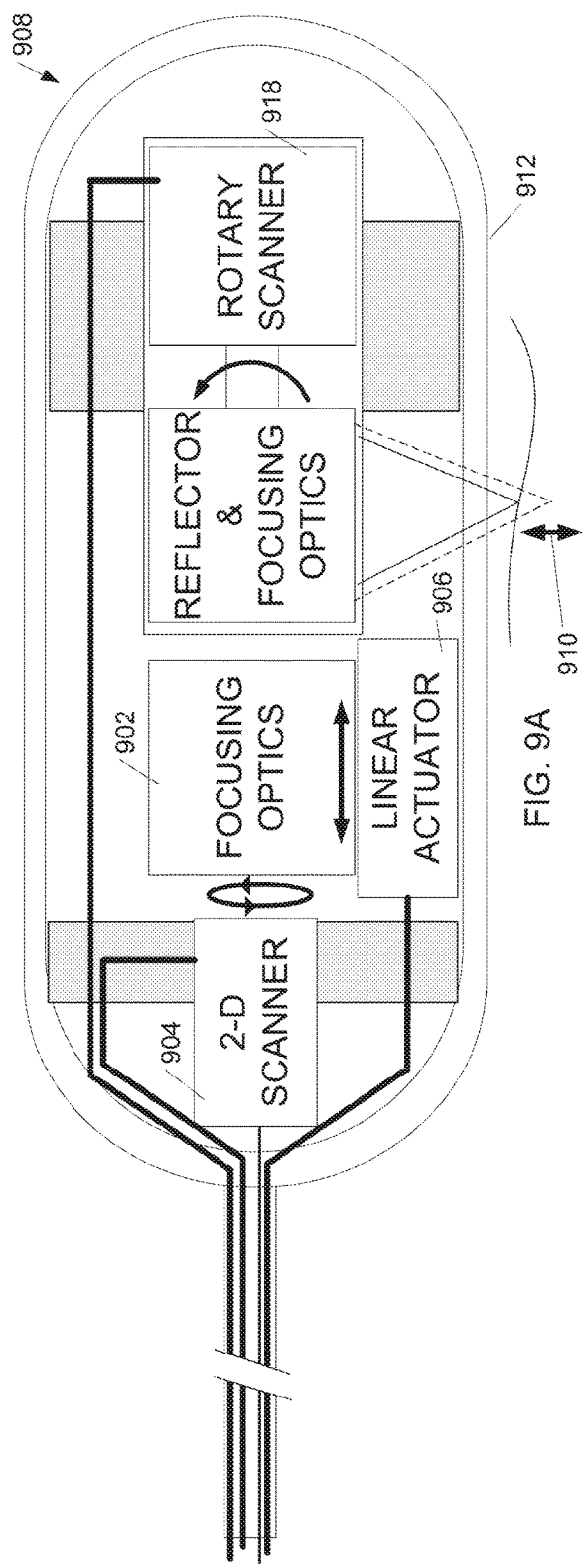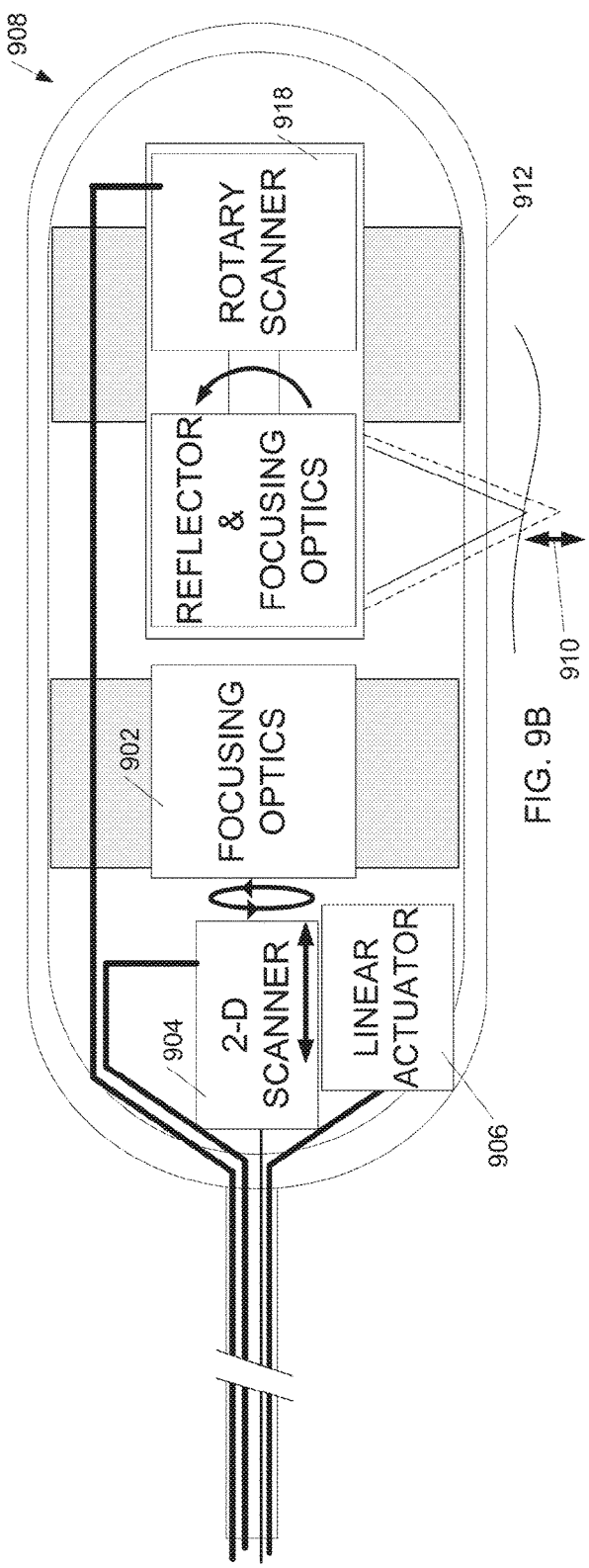

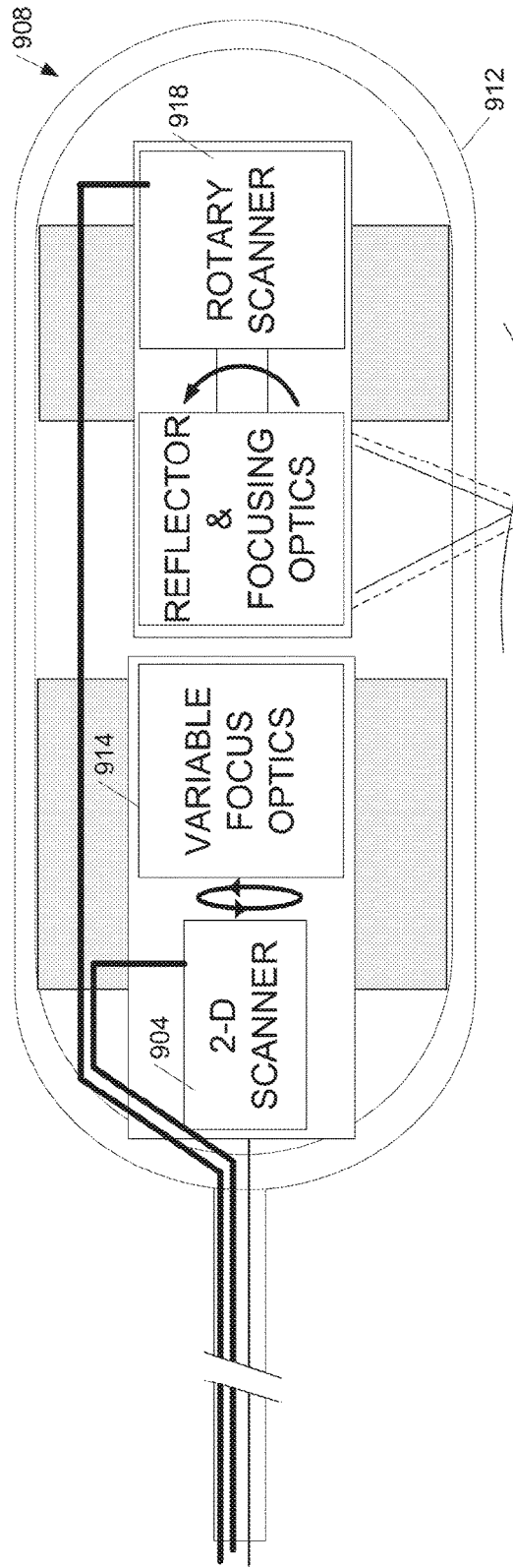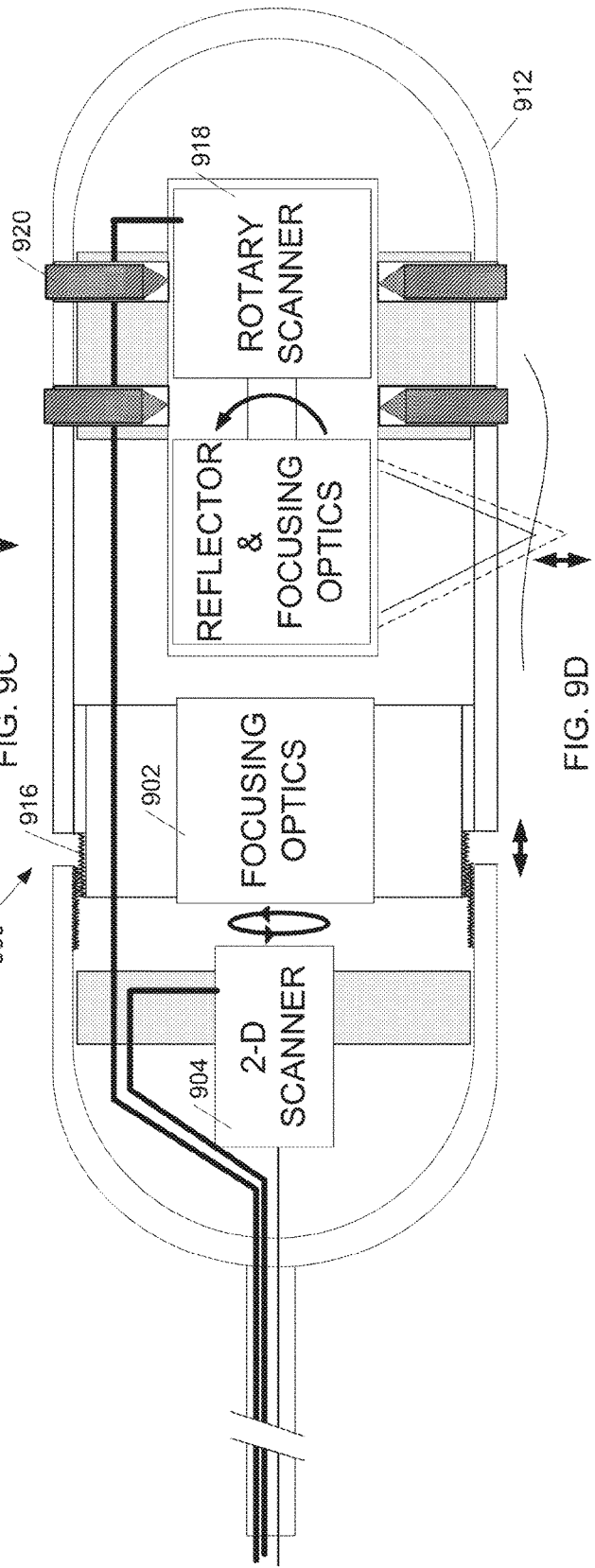

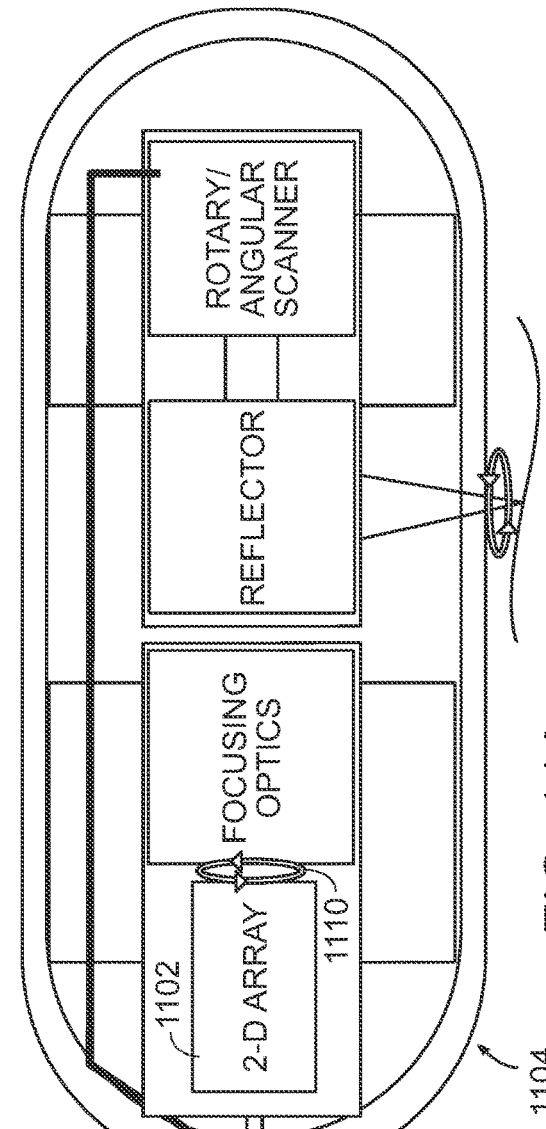
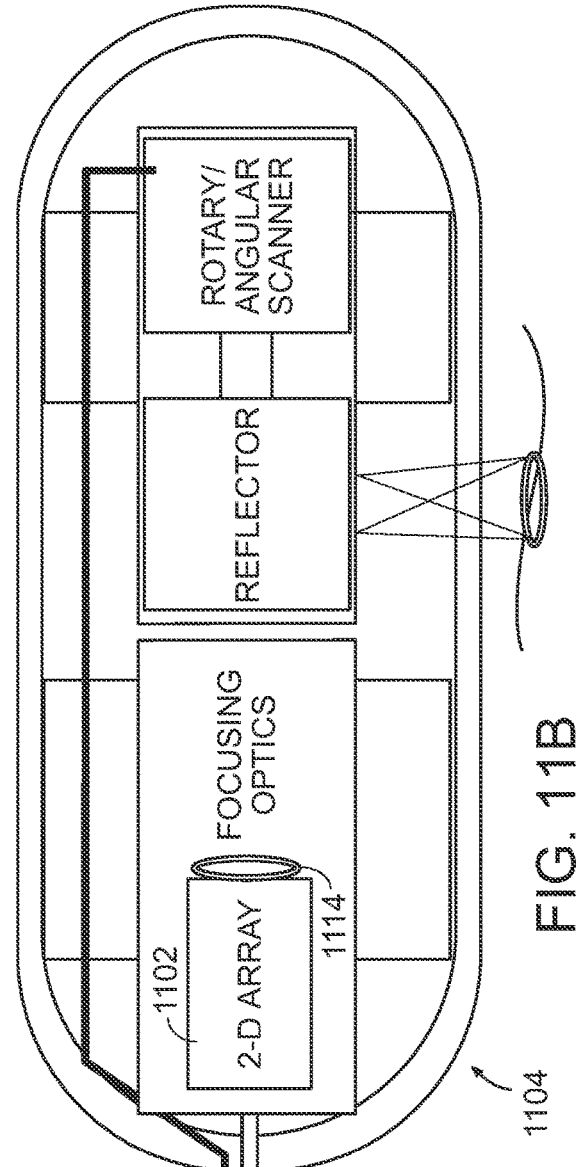
FIG. 11A
FIG. 11B

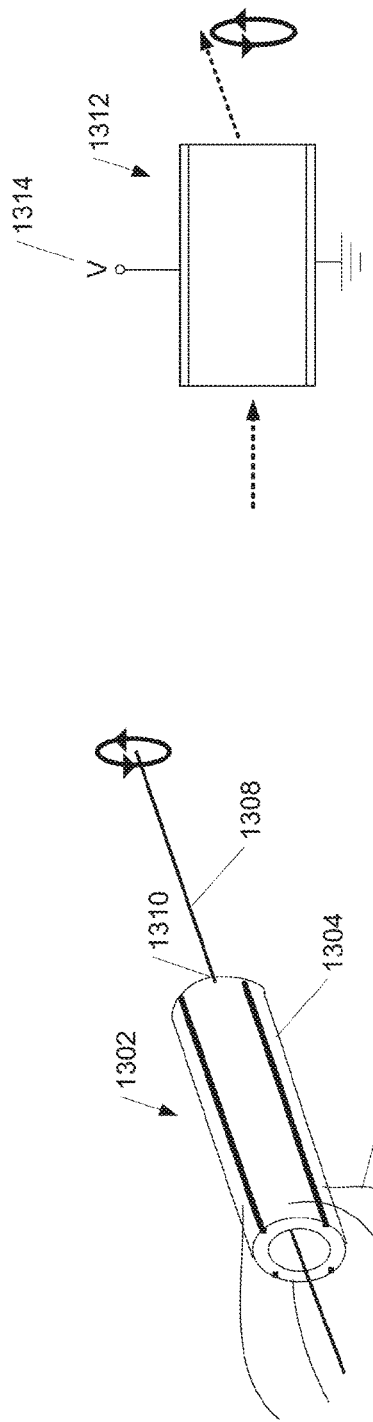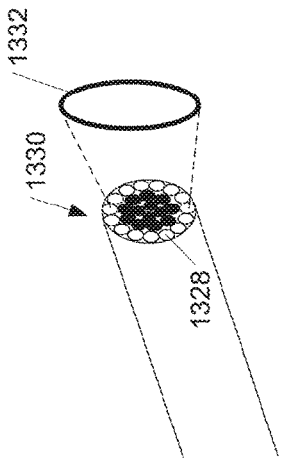
FIG. 13A
FIG. 13B
FIG. 13C
FIG. 13D
FIG. 13E

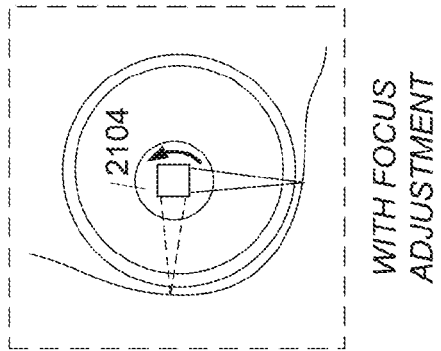
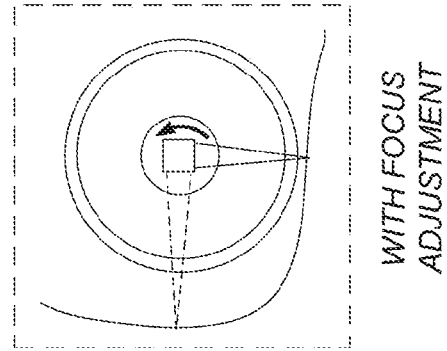
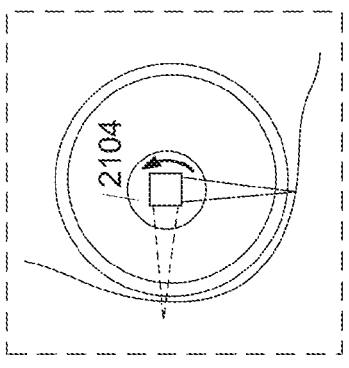
FIG. 21A
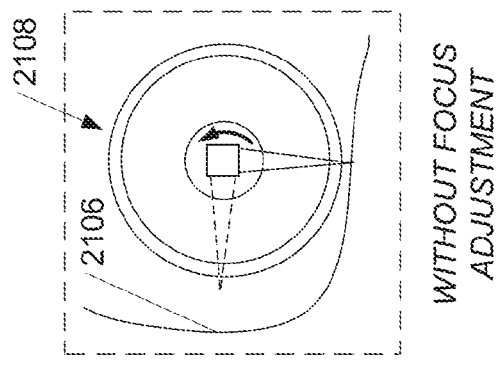
FIG. 21B
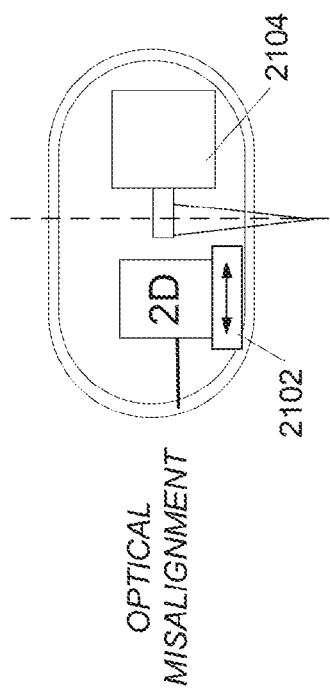
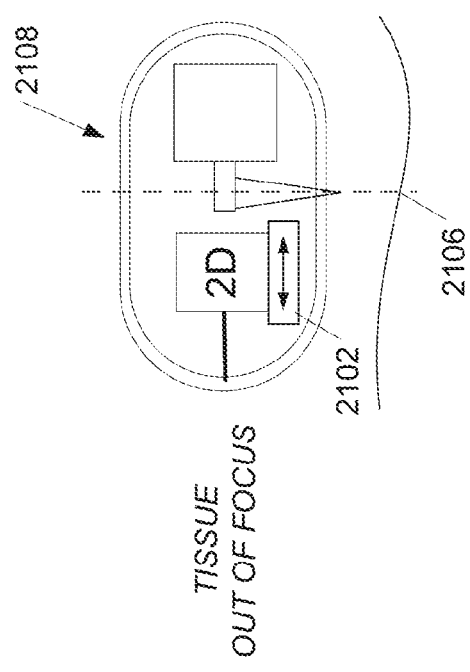

SCANNING OPTICAL IMAGING DEVICE

RELATED APPLICATION

This application is the U.S. National Stage of International Application No. PCT/US2018/030925, filed on May 3, 2018, which designates the U.S., published in English, and claims the benefit U.S. Provisional Application No. 62/501,365, filed on May 4, 2017. The entire teachings of the above applications are incorporated herein by reference.

GOVERNMENT SUPPORT

This invention was made with Government support under Grant Nos. R01 CA178636 and R01 CA075289 awarded by the National Institutes of Health and under Grant Nos. FA9550-15-1-0473 and FA9550-12-1-0499 awarded by the Air Force Office of Scientific Research. The Government has certain rights in the invention.

BACKGROUND

Real time imaging of luminal organs or surgical cavities in situ without tissue excision is important for disease surveillance, diagnosis, and treatment. Endoscopes are widely used in clinical practice to study the surface morphology and tissue structure of luminal walls, often at moderate resolution and magnification. However, structural features on the surface of the luminal wall typically provide insufficient clinical information. The gold standard for tissue examination in disease diagnosis is high resolution, micron-level microscopic imaging of excised tissue from a biopsy or resection, known as histopathology analysis, which assesses cellular features as well as depth of invasion in tissue. In order for real time imaging to approach the diagnostic capability of histopathology, techniques for in vivo microscopy and/or depth-resolved visualization are required.

Techniques such as confocal microscopy and optical coherence tomography (OCT) are emerging technologies for in vivo microscopic, volumetric imaging. However, confocal imaging has been largely limited to optical fiber bundle techniques that mostly image in the forward direction and are less used for the side-viewing direction, the latter being more ergonomic for luminal wall imaging. OCT imaging and scanning confocal imaging relies on optical beam scanning. 2-D scanning for in vivo imaging mostly depend on at least 1 mechanical actuation such as a rotation or linear pull-back outside of the patient to generate the slow axis scan. This type of external actuation known as "proximal" actuation is subject to motion artifacts and bends in the imaging catheter, and can produce an unstable scan trajectory. Unstable proximal scanning has a detrimental effect on image quality, especially at high imaging resolution. 2-D "distal" scanning methods such as the resonant spiral scan has had success in endoscopic imaging but is also limited to forward viewing. Techniques for 2-D distal scanning in the side viewing direction that are stable and highly repeatable are necessary for obtaining microscopic images for the diagnosis of luminal wall disease with technologies such as OCT, scanning fluorescence confocal microscopy, and other optical scanning microscopies. 2-D distal scanning is also useful for macroscopic imaging at low numerical aperture, by scanning quasi-collimated light over a large field of view and detecting reflected or fluorescent signals.

SUMMARY

An apparatus for optical imaging of a luminal organ or a surgical cavity comprises a proximal section, a distal section comprising a transparent portion, and a tether that connects the distal section to the proximal section. A two-dimensional (2-D) optical projector projects an optical beam in a 2-D closed curve optical pattern. Focusing optics receive the projected optical beam in the 2-D closed curve optical pattern and directs and focuses the light through the transparent portion of the distal section. A reflective scanner scans the projected optical beam focused by the focusing optics.

The proximal section may have a light source and the tether may comprise an optical waveguide that connects the light source to the 2-D optical projector. The optical waveguide may comprise multiple waveguide elements. The 2-D optical projector may comprise part of the optical waveguide. The 2-D optical projector may comprise multiple projector elements operating in parallel.

The 2-D optical projector may scan at a frequency that is 1000-10,000 times higher than the scan frequency of the reflective scanner. The reflective scanner may scan the projected optical beam over a length, at an outer surface of the transparent portion of the distal section, that is at least ten times a major dimension of the 2-D closed curve. In the case of a closed curve in the form of a circle, that major dimension is its diameter. An alternative closed curve is an ellipse of which the length of a major axis is less than 120% of a minor axis.

The 2-D optical projector may be a serial projector that is configured to perform rapid beam scanning in a 2-D closed curve. For example, the serial projector may perform rapid beam scanning at speeds exceeding 1 kHz. The serial projector may be a piezoelectrically actuated optical waveguide excited at our close to its resonance frequency.

The 2-D optical projector may alternatively be a parallel projector that is a 2-D optical array configured to project a pattern that is a 2-D closed curve.

The reflective scanner may be configured to perform slow beam scanning at speeds slower than 60 Hz. It may be a rotary scanner configured to perform slow beam scanning or an angular scanner configured to perform slow beam scanning over a limited range of angular deviations.

The combination of the 2-D optical projector and the reflective scanner may generate a cycloid trajectory and more specifically a prolate cycloid having loops.

The focusing optics may have low numerical aperture and an optical axis aligned with a longitudinal axis of the distal section. The focusing optics may comprise plural focusing optics elements and at least one focusing optics element may have high numerical aperture with focal distance smaller than a characteristic radius of a rigid enclosure. The focusing optics may have a focusing optics element with focal position relative to the distal section that is adjustable. The focusing optics may comprise variable focus optics to adjust the focal position of at least one focusing optics element The distal section may comprise section portions mated by a screw thread mechanism, and the 2-D projector and at least a portion of the focusing optics are on separate mated section portions whose separation distance can be adjusted by means of the threaded screw, which adjusts the focal position of the portion of the focusing optics.

The reflective scanner may be configured to be adjusted in centration, tilt or other position by a mechanical adjustment from outside of the distal section. The distal section may comprise a linear actuator to adjust the focal position of the focusing optics. The linear actuator may translate at least a portion of the focusing optics to adjust the focal position of the focusing optics. The linear actuator may translate a 2-D optical projector to adjust the focal position of the focusing optics. The focal position of the focusing optics may be determined by an angular position of the reflective scanner. The focal position of the focusing optics may be determined by the location of the sample being imaged relative to the distal section.

A light source may provide plural wavelengths and at least one of the wavelengths may be chosen for laser induced marking or ablation.

The outer housing of the distal section may have one or both of its ends shaped with a conical taper. The outer housing may be constructed of at least two materials, wherein at least one material is optically transparent and at least one material is optimized for a functional property other than optical transparency. A central portion of the distal section may have a diameter larger or smaller than the diameter of either end of the distal section. The distal section may include at least one static fiducial landmark.

A method for optical imaging of a luminal organ or surgical cavity may be performed using the described apparatus. The apparatus may be caused to scan an optical beam over a luminal organ or surgical cavity and acquire the optical image of the luminal organ or surgical cavity. The optical image may be processed and reconstructed according to the optical trajectory. An image may be reconstructed by mapping data points to Cartesian locations.

The distal section may be actuated by pulling or pushing the tether over a length that exceeds the width of the 2-D closed curve pattern to cover a large field of view. The reflective scanner may be controlled asynchronously with at least one other scanner in the distal section. The 2-D projector may be made to cease actuation as the reflective scanner positions the optical beam over a region of interest for laser induced ablation as indicated by the optical image. A portion of the 2-D closed curve optical pattern may be used to reconstruct the optical image. Multiple portions of the 2-D closed curve optical pattern may be used to separately reconstruct multiple optical images. The separately reconstructed multiple optical images may be further processed and then recombined to perform a single optical image. The multiple optical images may be acquired with different imaging modalities or imaging contrast by switching or modulating the light source wavelength, intensity or other parameter.

The focal position of the focusing optics may be controlled synchronously with position of the scanner. The focal position of the focusing optics may be controlled synchronously with the location of the sample being imaged. Reconstruction parameters may be based on location of a static landmark resulting from a static fiducial landmark in an acquired optimal image.

The optical beam may be projected in the 2-D closed curve multiple times between discrete steps of scan by the reflective scanner.

The reflective scanner may be rotated in alternate directions.

The present disclosure relates to an imaging device that scans an optical beam over a 2-D area in the side viewing direction. The device comprises at least one mechanism for projecting a 2-D optical pattern, also referred to as a 2-D optical projector, such as a 2-D scanner or 2-D optical array. The 2-D scanner is an electrical, piezoelectric, magnetic, electro-optic, acousto-optic or other type of actuator that is capable of rapid and continuous 2-D scanning. This scanner is fast and scans the optical beam rapidly in a 2-D closed curve with substantially equal length on orthogonal axes, such as a circle or an ellipse or a figure-of-eight (e.g. Lissajous) curve or other enclosed curve, over a relatively small scan length. The 2-D optical array is a 2-D array of optical sources such as a fiber bundle, a multi-core fiber, an array of light emitting diodes, an array of waveguides, or other optical array arranged in a 2-D closed curve. The device also comprises at least one other scanner that is slow, which is an electrical, hydraulic, pneumatic, piezoelectric, or other type of rotary scanner that scans at least a portion of the light from the 2-D scanner or 2-D array, slowly in a rotary direction around the circumference of the enclosure. Alternatively, the slow scanner may be a 1-dimensional (1-D) angular scanner such as an electrical, piezoelectric, galvanometric, microelectromechanical system (MEMS) or other type of angular actuator that scans an optical beam over a range of angular deviations covering a limited arc. This slow scan is a relatively large scan length. The combination comprising the 2-D optical projector and slow scanner results in the optical beam being scanned over a 2-D region around part of, or the entire circumference. The device may be a large diameter enclosure connected to a tether or catheter that is substantially smaller in diameter, or it may be a small diameter enclosure connected to or part of a tether or catheter that is similar in diameter. The enclosure is part of the "distal section", which is the end of the device that is more proximate to the subject or region being imaged, or located inside the subject body. The imaging engine to which the tether is connected is part of the "proximal section", which is the end of the device that is more proximate to the operator of the device and outside of the body of the imaging subject. The emitted light can be a single wavelength or a plurality of wavelengths, and the detected light can be reflected or fluorescent. Detected light can be transmitted via the same path as the emitted light, or via a different path such as a separate optical waveguide or a separate aperture of the same optical waveguide. This device and its related embodiments enable 2-D optical scanning and imaging to be performed within the luminal organs or surgical cavities of living subjects.

The disclosure also describes methods for accurately reconstructing the 2-D or 3-D image from the scan trajectory generated by the device. Some embodiments of the methods describe electronic synchronization of the multiple scanners in order to enable repeatable reconstruction. Some embodiments describe calibration methods for reconstruction when the scanners are asynchronous. Some embodiments describe exemplary reconstruction algorithms.

This class of devices could have substantial impact in clinical scenarios such as endoscopy or surgery, where rapid imaging of tissue lesions, surgical cavities, resection margins, or other regions of interest could provide real-time pathological information that might guide clinical decisions. The ability to generate precise, high resolution 2-D and 3-D imaging in vivo, particularly with fluorescence or other nuclear-level contrast, would further boost clinical utility of these devices in a broad range of diagnostic and therapeutic applications.

BRIEF DESCRIPTION OF THE DRAWINGS

The foregoing aspects and many of the attendant advantages of this disclosure will become more apparent by reference to the following detailed description, when taken in conjunction with the accompanying drawings, wherein:

FIG. 3 is a schematic view showing the device with the proximal section comprising an imaging engine connected to a tether, and the distal section placed within a body cavity;

FIG. 5A is a schematic view showing the distal section comprising a 2-D scanner and a rotary scanner, both of which are contained within the distal section, the 2-D scanner imparting motion or deflection to an optical waveguide or optical beam or other optical path, and the rotary scanner imparting motion to a reflector;

FIG. 5B is a schematic view of an exemplary optical system layout that could be used with the configuration of FIG. 5A, in which a set of focusing optics images the 2-D closed curve trajectory produced by the 2-D scanner on to the focal plane at a long working distance and low numerical aperture;

FIG. 5C is an alternate viewing perspective of FIG. 5B, showing the 2-D trajectory of the 2-D scanner projected as an annulus onto the focusing optics;

FIG. 9A is a schematic view showing a first set of focusing optics after the 2-D scanner being translated along the longitudinal axis of the distal section by a linear actuator, which has the effect of weakly focusing or weakly diverging the optical path prior to the second set of focusing optics for imaging, resulting in a translation of the focal plane;

FIG. 9B is a schematic view showing the 2-D scanner being translated along the longitudinal axis of the distal section by a linear actuator, which also has the effect of weakly focusing or weakly diverging the optical path prior to the focusing optics for imaging, resulting in a translation of the focal plane;

FIG. 9C is a schematic view showing the first set of focusing optics after the 2-D scanner having the ability to adjust their focal position, known as variable focus optics, which can be used to weakly focus or weakly diverge the optical path prior to the focusing optics for imaging, resulting in a translation of the focal plane;

FIG. 9D is a schematic view showing the distal section split into at least 2 portions with the 2-D scanner and rotary scanner in separate portions, with the at least two portions mated by screw threads, such that the separation distance between the 2-D scanner and the first set of focusing optics after the 2-D scanner can be manually adjusted with high precision, resulting in a translation of the focal plane, and the rotary scanner having set screw contacts for adjustable centration and tilt from the outside;

FIG. 11A is a schematic view showing the distal section comprising a 2-D optical array, and the imaging engine comprising a coherent light source such as a laser, and a 2-D scanner that scans an optical beam on to the proximal face of the 2-D array;

FIG. 11B is a schematic view showing the distal section comprising a 2-D optical array, and the imaging engine comprising an incoherent light source such as a light emitting diode and a 2-D camera sensor that detects the proximal end face of the 2-D array;

FIG. 13A-E are summaries of exemplary embodiments of 2-D optical projectors that generate a 2-D closed curve scan or 2-D optical pattern with a 2-D scanner, 2-D array or other means;

FIG. 21A is a schematic showing an embodiment of a method to adjust the focus of the optical system around the circumference of the distal section to compensate for optical misalignment;

FIG. 21B is a schematic showing an embodiment of a method to adjust the focus of the optical system based on the location of the tissue sample being imaged;

DETAILED DESCRIPTION

Figure 1A:
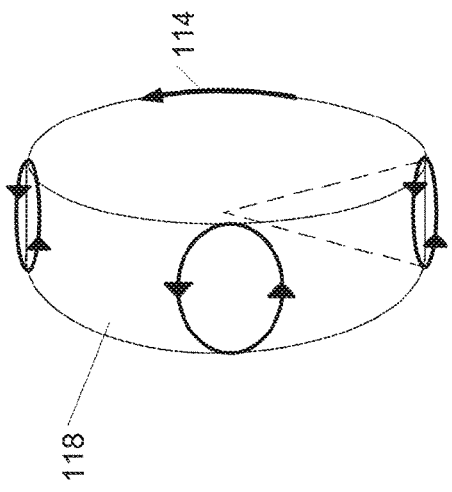
FIG. 1A-B are schematics showing a 2-D projector that is a 2-D scanner or 2-D optical array, and a rotary or angular scanner combining to generate a side viewing optical scan over a 2-D tubular region.
Figure 1B:
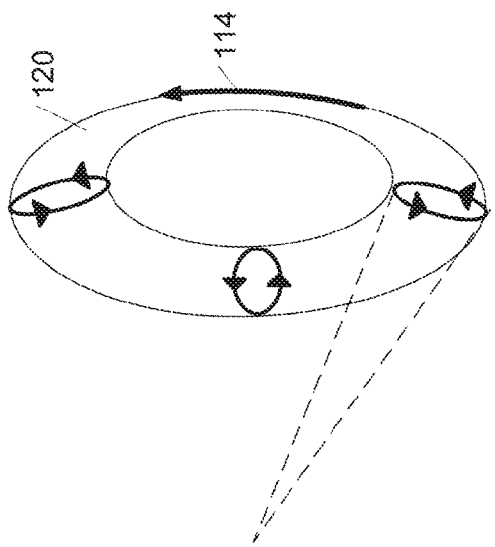
Figure 1C:
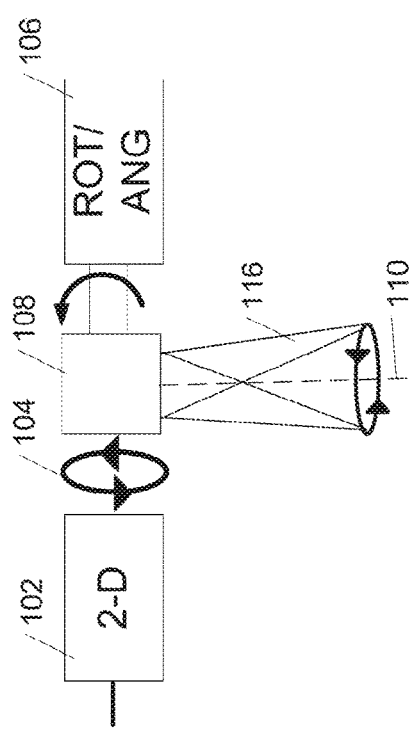
FIG. 1C-D are schematics showing a 2-D scanner or array, and a rotary or angular scanner generating a scan over a 2-D conical region.
Figure 1D:
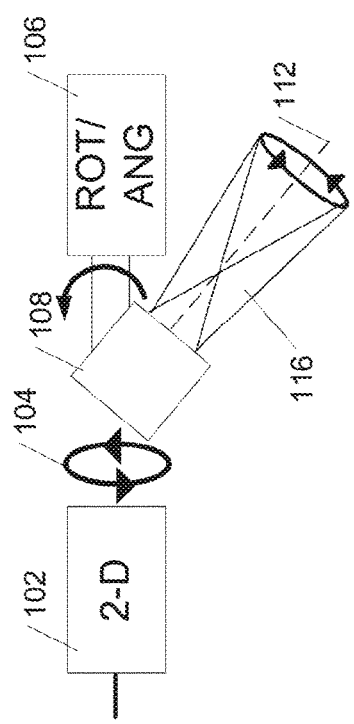

FIG. 1 shows schematics of some embodiments of the device and the optical scan trajectory that is generated. The device uses at least one 2-D projection mechanism, also referred to as a 2-D optical projector, that rapidly projects a 2-D closed curve optical pattern in the form of a single composite optical beam, such as a 2-D scanner or a 2-D optical array. A 2-D scanner projects a rapidly moving optical beam continuously, and can be referred to as a serial projector. The rapidly moving optical beam in a 2-D closed curve has the effect of forming a single composite beam. When the 2-D closed curve pattern is circular or elliptical, the composite beam is annular. A 2-D optical array projects a set of multiple stationary optical beams simultaneously, and can be referred to as a parallel projector. The set of multiple beams has the effect of forming an annular composite beam when the 2-D closed curve pattern is circular or elliptical. A 2-D scanner is an actuator that is capable of steering an optical waveguide in a 2-D trajectory, such as a piezoelectric actuator in a tubular or other form, or a microelectromechanical system (MEMS) based actuator, or an actuator that is capable of producing 2-D deflection of an optical beam such as a crystal-based optical deflector or other electro-optic or acousto-optic deflector. In the embodiment that uses a piezoelectric tubular actuator, an optical waveguide may be passed through the center of the piezoelectric tube and mounted to the tube tip, such that electrically exciting the tube generates physical deflection of the tube and the optical fiber, resulting in an optical scan. A 2-D optical array is an array of optical sources such as a fiber bundle, a multi-core fiber, an array of light emitting diodes, an array of waveguides, or other optical array. Detected optical signals are collected via the same waveguide for illumination or a separate optical path via an adjacent waveguide or other optical path. The 2-D scanner or array 102 continuously projects a 2-D closed curve 104 such as a circle, an ellipse with major and minor axes of substantially equal length, a figure-of-eight (e.g. Lissajous) curve, or other similar 2-D closed curve. For the scan to be sufficiently large amplitude, the scanner or the waveguide being actuated by the scanner may be in a mechanically resonant state. The 2-D closed curve pattern 104 typically has a relatively small diameter or size. The device also uses at least one scanner 106 that moves substantially slower than the 2-D scanner. In a set of embodiments, this slow scanner is capable of continuous rotary scanning, such as an electric, piezoelectric, hydraulic, pneumatic or other rotary actuator. The rotary scanner rotates a reflector 108 such a substantially 45 degree angled prism, polygonal prism, or other reflector that reflects the 2-D closed curve pattern to an axis 110 at substantially 90 degrees, or an axis 112 at an acute angle pointing forward or backward relative to the longitudinal axis of the distal section. The rotary scanner can alternatively rotate a set of focusing optics including at least one reflector 108 and serving as the imaging objective for imaging at higher numerical aperture. In embodiments where the reflection is at substantially 90 degrees, the rotary scanner causes the center axis 110 of the 2-D closed curve pattern to trace out a large circle. In embodiments where the reflection is at an acute angle pointing forward or backward, the center axis 112 of the 2-D closed curve scan traces out a large cone. In another set of embodiments, this slow scanner 106 is a 1-dimensional (1-D) angular actuator such as an electric, piezoelectric, galvanometric, MEMS or other angular actuator that tilts a reflector over a range of angular deviations. The scanner can be driven with a sawtooth or triangular trajectory. The rotary or angular scanner typically scans the optical beam over a relatively large scan length 114. The optical beam 116 is typically projected by the 2-D scanner or array first, then scanned by the rotary or angular scanner. The relatively slow rotary or angular periodic scan of the 2-D curve pattern results in optical scanning over a 2-D rectangular strip 118 or conical area or region 120 around part of or the entire circumference. The optical beam 116 can contain a single wavelength or a plurality of wavelengths depending on the light source and the imaging modality. The wavelengths can be emitted simultaneously, sequentially, or modulated. In FIG. 1A-B, the combination of the 2-D projector 102 and rotary actuator 106 with the reflection at 90 degrees generates a scan over a 2-D area of tubular geometry 118. In FIG. 1C-D, the angled reflection pointing forward (or backward) generates a conical area scan 120. In embodiments where an angular scanner is used, a 2-D area scan over a limited angular sector is generated. For sufficiently dense scanning over the 2-D region, the rotary or angular scanner is substantially slower than the 2-D scanner. Due to the reflector having the well-known mirror reflection property of inverting/reversing an image in the axis normal to its surface, it imparts a slow rotation to the 2-D closed curve pattern about its own center while the slow rotary or angular actuator scans. Therefore a line scan or other 1-D scan or a substantially elliptical pattern impinging on the reflector does not generate a raster-like scan and would not scan completely over a 2-D strip region when scanned by the rotary or angular scanner. The 2-D projector should project a 2-D pattern that is substantially large and equal length on 2 orthogonal axes, wherein it is advantageous that the major axis of the 2-D pattern is less than but not limited to 120% length of the minor axis, such as a circle, ellipse, figure of eight, or other similar closed curve pattern.

For a generalized closed curve generated by the 2-D projector and translated by the rotary or angular scanner, the equations defining the trajectory unfolded onto a flat xy plane are as follows:

$$\begin{bmatrix} x \\ y \end{bmatrix} = Rot(\theta) \cdot \begin{bmatrix} h_x(t) \\ h_y(t) \end{bmatrix} + \begin{bmatrix} 0 \\ 2\pi R f_{slow} t \end{bmatrix} \quad (0)$$

where $h_x(t)$ and $h_y(t)$ are parametric equations for the 2-D closed curve. The closed curve must have the property that it is substantially large and equal length on two orthogonal axes. Without loss of generality, assume that the closed curve is a circle:

$$\begin{bmatrix} x \\ y \end{bmatrix} = Rot(\theta) \cdot \begin{bmatrix} \sin(2\pi f_{fast}t) \\ \cos(2\pi f_{fast}t) \end{bmatrix} + \begin{bmatrix} 0 \\ 2\pi R f_{slow}t \end{bmatrix} \quad (0)$$

$f_{fast}$ and $f_{slow}$ are the frequencies or speeds of the 2-D projector and the rotary or angular scanner respectively, and R is the radius of the distal section. If the 2-D projector is a 2-D scanner, $f_{fast}$ is the repetition frequency or resonance frequency of the 2-D scanner. If the 2-D projector is a 2-D optical array and the optical detection is performed by a camera sensor, then $f_{fast}$ is the camera frame rate. Rot(θ) is a rotation due to the mirror inversion that is determined by the angular position of the rotary or angular scanner, and the sign of the rotation angle θ is determined by the direction of actuation (clockwise or counterclockwise) of the rotary or angular scanner. The equations can be expanded as follows:

$$\begin{bmatrix} x \\ y \end{bmatrix} = \begin{bmatrix} \cos(\theta) & -\sin(\theta) \\ \sin(\theta) & \cos(\theta) \end{bmatrix} \begin{bmatrix} \sin(2\pi f_{fast}t) \\ \cos(2\pi f_{fast}t) \end{bmatrix} + \begin{bmatrix} 0 \\ 2\pi R f_{slow}t \end{bmatrix} \quad (0)$$

$$= \begin{bmatrix} \cos(2\pi f_{slow}t + \phi) & -\sin(2\pi f_{slow}t + \phi) \\ \sin(2\pi f_{slow}t + \phi) & \cos(2\pi f_{slow}t + \phi) \end{bmatrix} \begin{bmatrix} \sin(2\pi f_{fast}t) \\ \cos(2\pi f_{fast}t) \end{bmatrix} + \begin{bmatrix} 0 \\ 2\pi R f_{slow}t \end{bmatrix}$$

$$= \begin{bmatrix} \sin(2\pi(f_{fast} - f_{slow})t - \phi) \\ \cos(2\pi(f_{fast} - f_{slow})t - \phi) \end{bmatrix} + \begin{bmatrix} 0 \\ 2\pi R f_{slow}t \end{bmatrix}$$

The only undetermined parameter is φ, which defines the initial angular position of the rotary or angular scanner at t=0, and will be further discussed under reconstruction methods. The geometric curve resulting from this particular embodiment of scan trajectory is called a prolate cycloid, and is part of the trochoid curve family. This embodiment of scan trajectory is referred to as a cycloid scan.

Figure 2A:
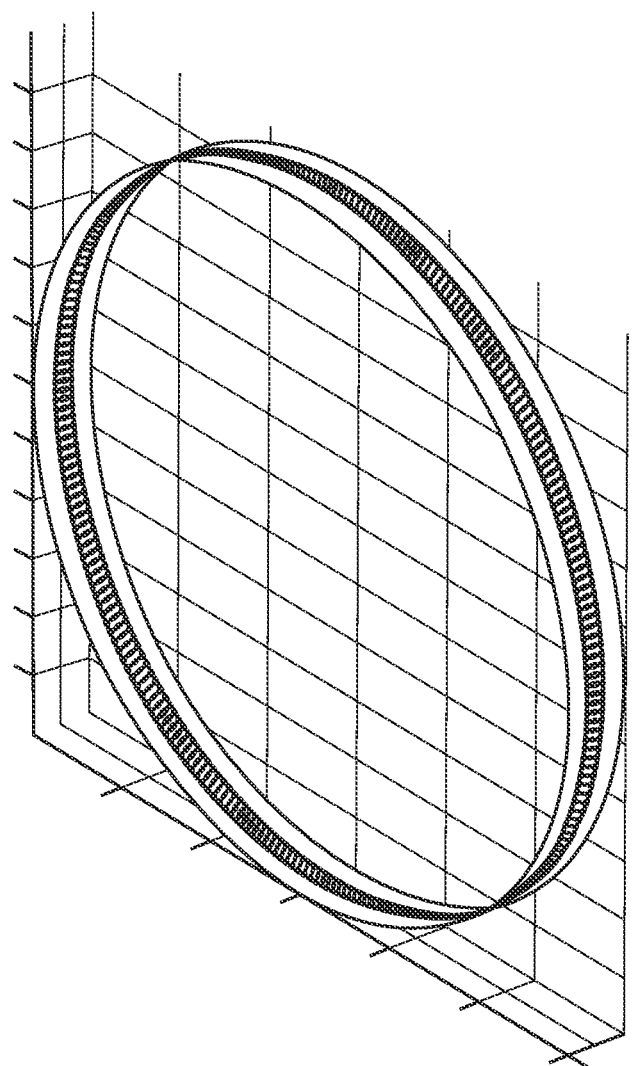
FIG. 2A is a schematic view showing the optical trajectory in 3-D that is produced by the combination of the 2-D scanner or array and rotary scanner.
Figure 2B:
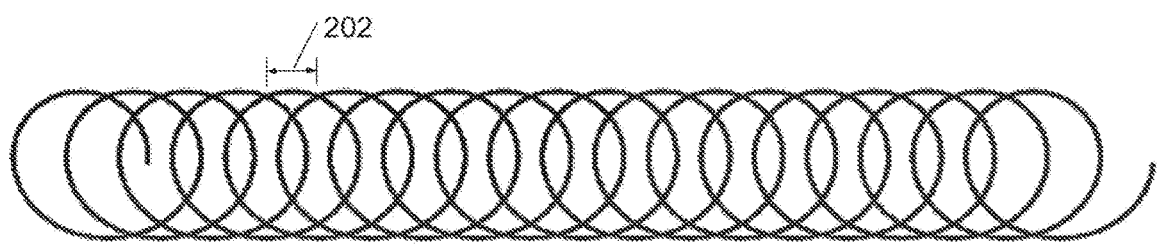
FIG. 2B is a schematic view showing the scan trajectory when unwrapped onto a flat plane, with a small number of circles for illustrative purpose.
Figure 2C:
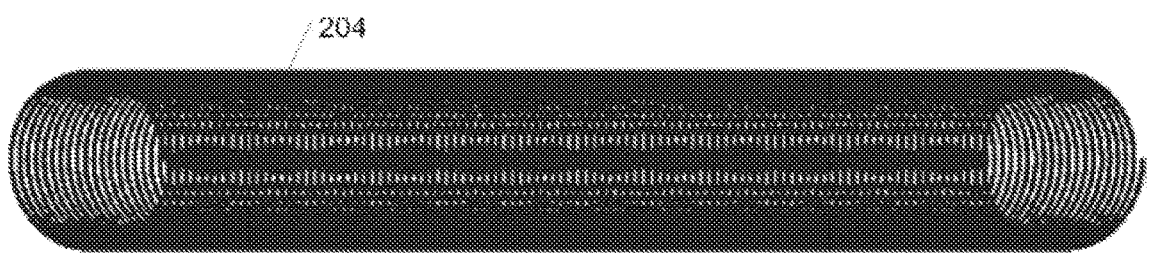
FIG. 2C is a schematic view showing the unwrapped scan trajectory with a large number of circles for dense optical sampling.

FIG. 2A-C show embodiments representing the optical trajectory that is generated by the combination of the 2-D scanner or array and the rotary or angular scanner. FIG. 2A shows the scan trajectory in 3-D space as a strip in a tubular geometry when a 2-D scanner or array produces a circular pattern and a rotary scanner provides the slow scan. FIG. 2B shows the trajectory when unfolded on to a flat plane and sparsely sampled for illustrative purposes. Sparse sampling occurs when $f_{slow}$ is not substantially smaller than $f_{fast}$, resulting in a large spacing or pitch 202 between each 2-D pattern. Sparse sampling such as sampling that does not meet the Nyquist sampling criteria may be chosen by design for more rapid imaging at the expense of image quality. FIG. 2C shows the unfolded trajectory when densely sampled. Dense sampling occurs when $f_{slow}$ is substantially smaller than $f_{fast}$, resulting in a small spacing or pitch 204 between each adjacent 2-D pattern. Sampling may attain or exceed the Nyquist criteria if desired, the latter being required for OCT angiography or other imaging modalities.

This type of scan trajectory is different from the raster or helical scan of previous side-viewing optical scanning devices or the spiral scan of previous forward-viewing devices. When the 2-D closed curve scan is a circle, the resultant trajectory is known as a prolate cycloid. For optical imaging applications, in order to acquire image data without loss of resolution set by the optical spot size, the separation between individual samples along a particular direction is determined by the Nyquist criteria. For the fast 2-D closed curve scan that is a circle, the number of samples $N_{Nyquist}$ in one period can be calculated as:

$$N_{Nyquist} = 2 \times \frac{\pi D}{\omega} = \frac{S}{f_{fast}} \quad (0)$$

where D represents the diameter of the 2-D circle in the imaging plane (also the width of the scanned 2-D region), w represents the spot size or transverse resolution of the optical imaging system, S represents the data sampling rate and $f_{fast}$ represents the frequency of the 2-D scanner. Alternatively this may also be represented independent of the optical magnification in terms of the deflection d of the optical waveguide or optical path and the mode field diameter w of the waveguide or beam:

$$2 \times \frac{\pi d}{w} = \frac{S}{f_{fast}} \quad (0)$$

Similarly for the slow rotary or angular scan direction, the number of samples $M_{Nyquist}$ can be calculated as:

$$M_{Nyquist} = 2 \times \frac{C}{\omega} = \frac{f_{fast}}{f_{slow}} \quad (0)$$

where C represents the length of the scanned circumference or sector of the distal section encompassed by the rotary or angular scanner, and $f_{slow}$ represents the frequency of the rotary or angular scanner. This calculation neglects the fact that the circular scan generates 2 separate semicircular line scans defined by the two halves of the circle, which results in a rescanning effect. This will be discussed in further detail later. The ability of 2-D scanners such as piezoelectric or electro-optic actuators to move as fast as tens of kHz, camera sensors to image at >100 kHz, and the ability of rotary or angular scanners to actuate at speeds of a few Hz to tens of Hz at high precision enables extremely high speed and repeatable imaging.

For optical coherence tomography imaging an exemplary A-scan rate would be S=1,000,000 (1 MHz) for state of the art OCT instruments. For D=1 mm and ω=30 µm, one requires a fast scan frequency of ~4800 Hz. For C=40 mm, the slow scan frequency is ~2 Hz. Although this example is presented assuming an A-scan rate of 1 MHz, it is noted the OCT imaging can be performed at different rates which can be 50 kHz to several MHz. Imaging with scanning confocal microscopy may be performed at rates as fast as tens of MHz or higher; an exemplary sampling rate would be S=10,000,000 (10 MHz), and exemplary parameters D=0.5 mm, ω=2 µm, and C=40 mm require a fast scan frequency of ~6400 Hz and a slow scan frequency of ~0.17 Hz. It is also noted that the circumference and spot size may be different depending on the application. Although the Nyquist criteria provides general guidelines for imaging, variations from the above mentioned examples are possible depending on the resolution and image acquisition time requirements of the application. For example, for certain imaging modalities such as Doppler OCT or OCT angiography, one requires oversampling compared to the Nyquist criteria with time separation between samples. For the OCT example given previously, OCT angiography would require an oversampling of up to ~5× in the rotary direction between sequential circular scans, which requires a lower rotation frequency of ~0.4 Hz. Denser/sparser samples compared to Nyquist criteria may also be acquired in order to perform averaging to increase image quality and/or to increase imaging speed for overcoming motion artifacts and/or to perform an initial preview or scout scan to identify regions of interest for further interrogation and/or for calibrating/determining acquisition parameters or settings, and/or confirming the positioning of the imaging device at a desired location. It is advantageous for the scan frequency of the 2-D scanner, $f_{fast}$ to be in the range of but not limited to >1 kHz. It is advantageous for the scan frequency of the rotary or angular scanner $f_{slow}$ to be in the range of but not limited to <60 Hz, which is close to modern video frame rates.

FIG. 3 is a schematic illustration showing the device, with a distal section 302 connected by a tether 304 to the proximal section 306 comprising an imaging engine 308. The imaging engine 308 comprises one or more light sources 310, detectors and controllers 312, data acquisition hardware and processors 314, depending on the imaging modality. The light 310 from the imaging engine 308 may be single wavelength, or a plurality of wavelengths for imaging, marking, ablation, or other purposes that are emitted simultaneously, sequentially or modulated. The light 310 can also be of a single or multiple or modulated polarizations. For optical coherence tomography (OCT), the light source 310 can be a swept wavelength laser or a broadband optical source, and the detector 312 can be a balanced photodetector or spectrometer. For confocal microscopy or fluorescence imaging or nonlinear imaging, the light source 310 can be a continuous wave or pulsed laser, and the detector 312 can be a photomultiplier tube, avalanche photodiode or other high sensitivity optical detector. For embodiments where the 2-D projector in the distal section 302 is a 2-D array, the detector 312 can be a camera sensor. The light sources 310 and detectors 312 are connected to the distal section 302 of the device by at least one optical waveguide or fiber contained within the tether 304. The waveguides can carry the source light and return light in the same optical path, such as in a single mode or multimode fiber, or it can use separate optical paths for portions of the source light and return light, such as in a dual clad fiber or multicore fiber. The imaging engine 308 can contain linear and/or rotary scanners or actuators 316 for linearly pulling or pushing, or rotating portions of the tether 304 for scanning the optical beam in the distal section 302 of the device. The controllers 312 produce electrical/electronic waveforms that are used to control the scanners 316 in either the distal section 302 or the proximal section 306 of the device, and can be synchronous or asynchronous to the data processors 314. The controllers 312 are connected to the distal section 302 of the device by one or more electrical connections contained within the tether 304. The data acquisition hardware and processors 314 acquire imaging raw data and process or reconstruct data for display or storage.

Figure 4A:
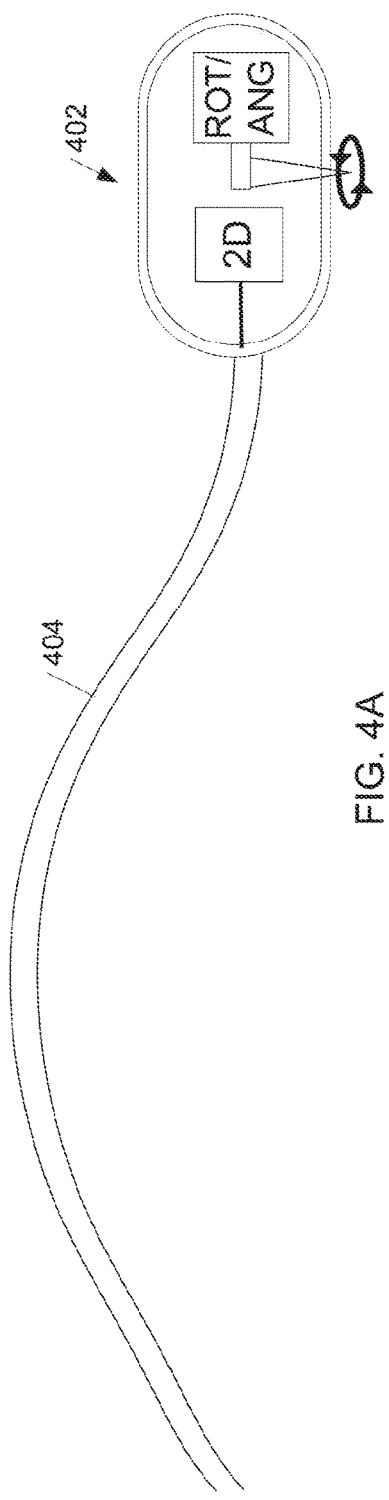
FIG. 4A is a schematic view showing the distal section with the 2-D projector and scanner contained in a tethered section that has diameter substantially larger than the tether.
Figure 4B:
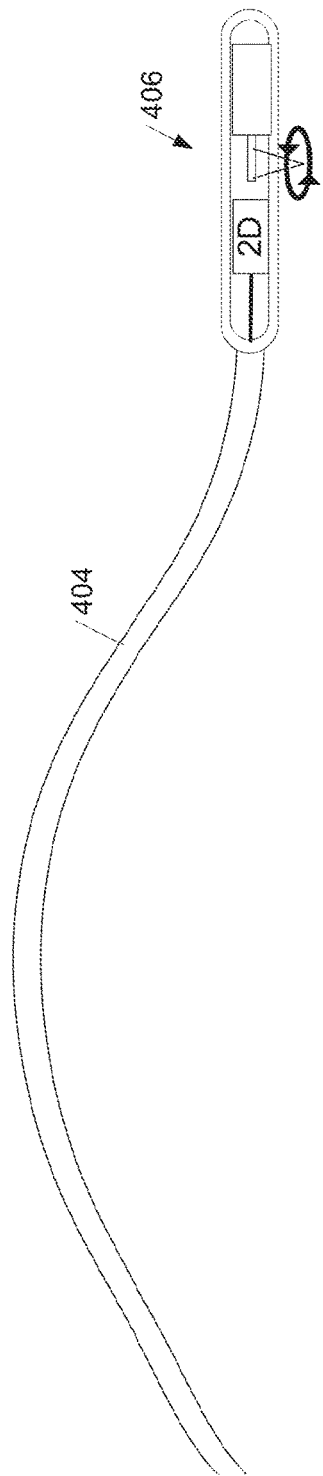
FIG. 4B is a schematic view showing the distal section as a tethered section that has diameter marginally larger than the tether.
Figure 4C:
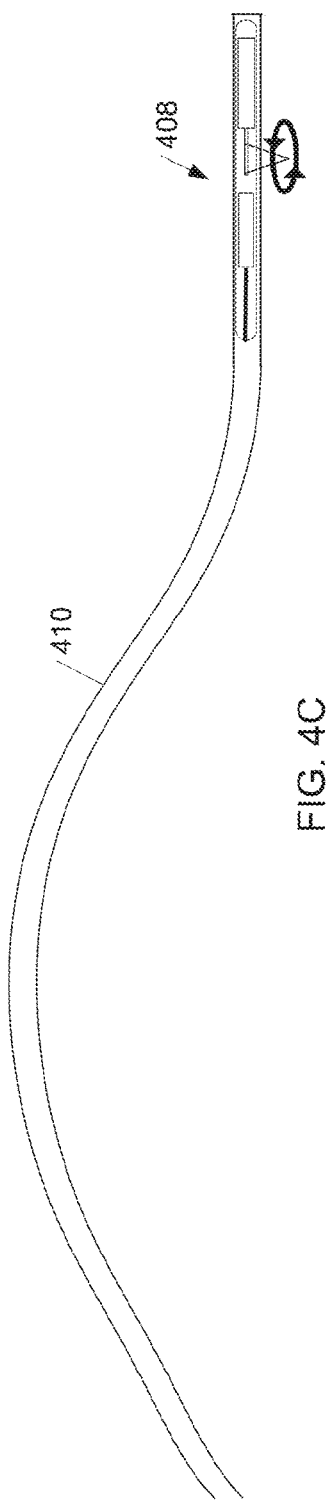
FIG. 4C is a schematic view showing the distal section with the scanners contained within a tether or sheath.

FIG. 4A-C are schematic illustrations showing the proposed device in three exemplary embodiments of the size of the distal section relative to their tethers. The tether connects the distal section to the imaging engine, and contains one or more optical waveguides and one or more electrical cables. The tether can be flexible to optimize patient comfort when the distal section is swallowed by a conscious patient, or it can be semi-rigid or more rigid to optimize positioning and other ergonomic control of the distal section by the operator. The distal section is transparent at least in part, to permit transmission of the optical beam. In FIG. 4A, the distal section 402 is substantially larger diameter than the tether 404. This embodiment is useful for the imaging of a relatively large organ lumen such as the esophagus that has inner diameter approximately in the range of but not limited to 10-20 mm, where it is necessary for the distal section to achieve substantial physical contact or proximity with the organ lumen for sufficient imaging coverage. The distal section 402 may be swallowed by a conscious patient similar to a pill or capsule, or it may be introduced into the esophagus of a sedated patient by a clinician. In FIG. 4B, the distal section 406 is smaller than in the embodiment of FIG. 4A, and of similar and slightly larger diameter compared to the tether 404. This embodiment is useful for the imaging of relatively smaller organ lumens, minimally invasive surgical cavities, imaging in pediatric patients, or other scenarios in which a smaller distal section is advantageous. In FIG. 4C, the distal section 408 is completely encapsulated by a tether or sheath 410 that is transparent at least in part, such that the device is a catheter. This embodiment is useful when the device is introduced into the accessory channel of an endoscope that has inner diameter approximately in the range of but not limited to 2-6 mm, or is otherwise required to have minimal form factor for ergonomic purposes or due to other practical constraints.

Figure 6:
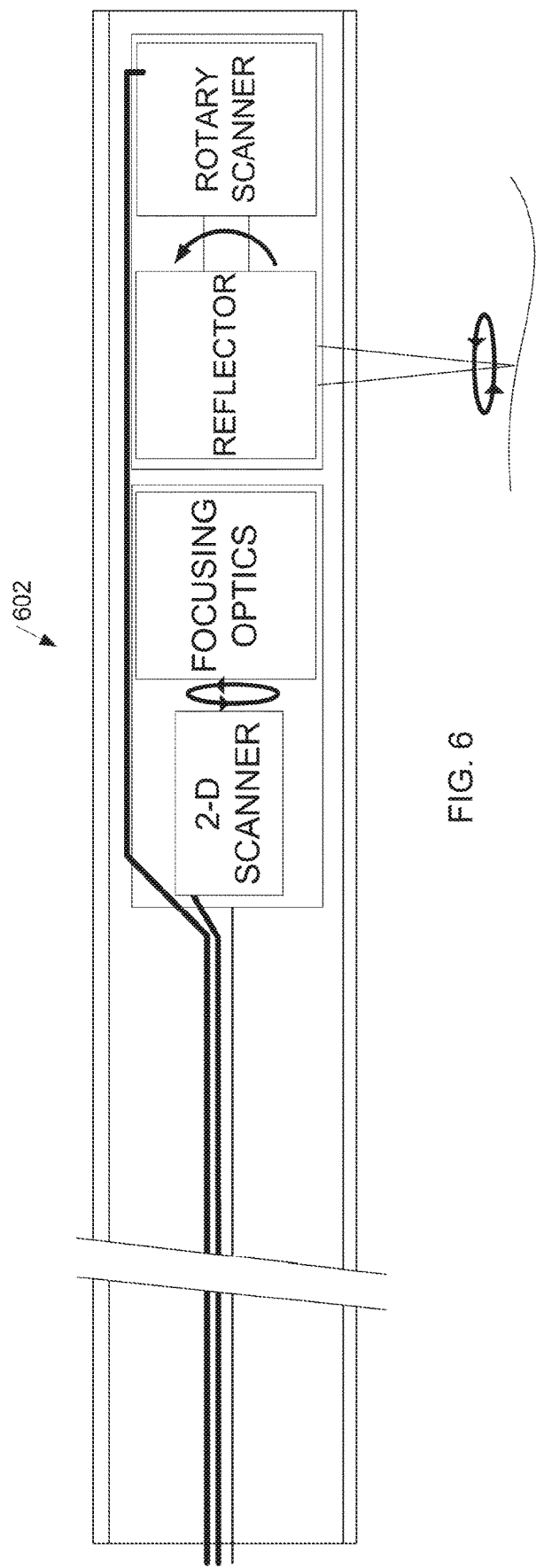
FIG. 6 is a schematic view showing the embodiment of FIG. 5, i.e. the combination of a 2-D scanner and a rotary scanner actuating a reflector, in the compact form of FIG. 4C that is enclosed within the tether.

FIGS. 5 to 11 show embodiments of the device that combine at least one 2-D scanner or array with at least one or more scanners or actuators, for imaging by a detector in the imaging engine of the proximal section. In embodiments that depict the 2-D projector being either a 2-D scanner or a 2-D array, there can also be embodiments in which the other is substituted. The disclosure in part describes 2-D optical scanning that is generated by two or more scanners that are contained within the distal section and are known as 'distal scanners'. This is in contrast to some embodiments of optical scanning for medical imaging that require one or more scanners located much closer to the proximal section outside of the body of the subject being imaged, which are known as 'proximal scanners'. Proximal scanning of the optical beam can be prone to non-uniform motion due to bends in the catheter or tether as well as patient-related motion. Distal actuation methods produce more stable and repeatable scan trajectories. In FIG. 5, the focusing optics 502 in front of the 2-D scanner 504 produce a focusing beam 506 that has a relatively long working distance to the focal plane and low numerical aperture. For example, at 1300 nm wavelength, numerical aperture of 0.05 and Gaussian waist ($1/e^2$) size of 30 µm in the focal plane, the confocal depth of field at the focus is ~1 mm. FIG. 5A shows a schematic of an exemplary embodiment, and FIG. 5B shows an exemplary optical system layout. An optical waveguide or fiber 508 delivers light from the imaging engine. The 2-D scanner 504 generates a circular scan or other 2-D closed curve trajectory 506. The 2-D closed curve scan 506 impinges upon a set of focusing optics 502 such as a gradient index lens or a convex lens or other focusing elements. If the optical waveguide or fiber 508 is being mechanically actuated by the 2-D scanner 504, the optical fiber 508 may have a focusing optic 502 on its tip such as a curved or lensed tip produced by a splicer or other fiber shaping tool. The focusing beam impinges upon a reflector 510 such as a prism or tilted mirror or other reflector, which is mounted to the center axis of a rotary scanner 512. The reflector 510 can be a deformable mirror or a curved mirror, which can reduce optical aberrations and improve the performance of the optical system. In some embodiments, both the focusing optics 502 and the reflector 510 can be mounted to the rotary scanner 512 for rotation. In some embodiments, both the focusing optics 502 and the reflector 510 can be part of a single monolithic optical component. The reflector 510 directs the 2-D trajectory 506 at substantially 90 degrees or at an acute angle forward or backward relative to the longitudinal axis of the distal section 514, such that the focal plane lies at the outer surface 516, or a short distance away from the outer surface 516, or a further distance away from the outer surface 516. The slow rotation of the rotary scanner 512 allows the 2-D closed curve 518 at the focal plane to trace out a 2-D strip region in a tubular or conical geometry that concentrically surrounds the distal section 514. Having the 2-D trajectory at an angular tilt relative to the longitudinal axis results in a tilted focal plane, which can be beneficial for covering a range of imaging depths. The scanners are connected to the imaging engine by at least one electrical cable 520. FIG. 5C is another viewing perspective of FIG. 5B, which shows the expanding optical beam 522 from the optical fiber 508 trace out a 2-D annular composite beam 524 on the face of the focusing optics 502, in embodiments where the 2-D closed curve is a circle or ellipse, and the focusing optics 502 is separate from the 2-D scanner 504. The embodiment presented in FIG. 6 is the embodiment of FIG. 5 that has been designed for a smaller form factor 602, such as described in FIG. 4C. This particular embodiment can be compatible with the accessory channel of an endoscope, or used in minimally invasive scenarios.

Figure 7:
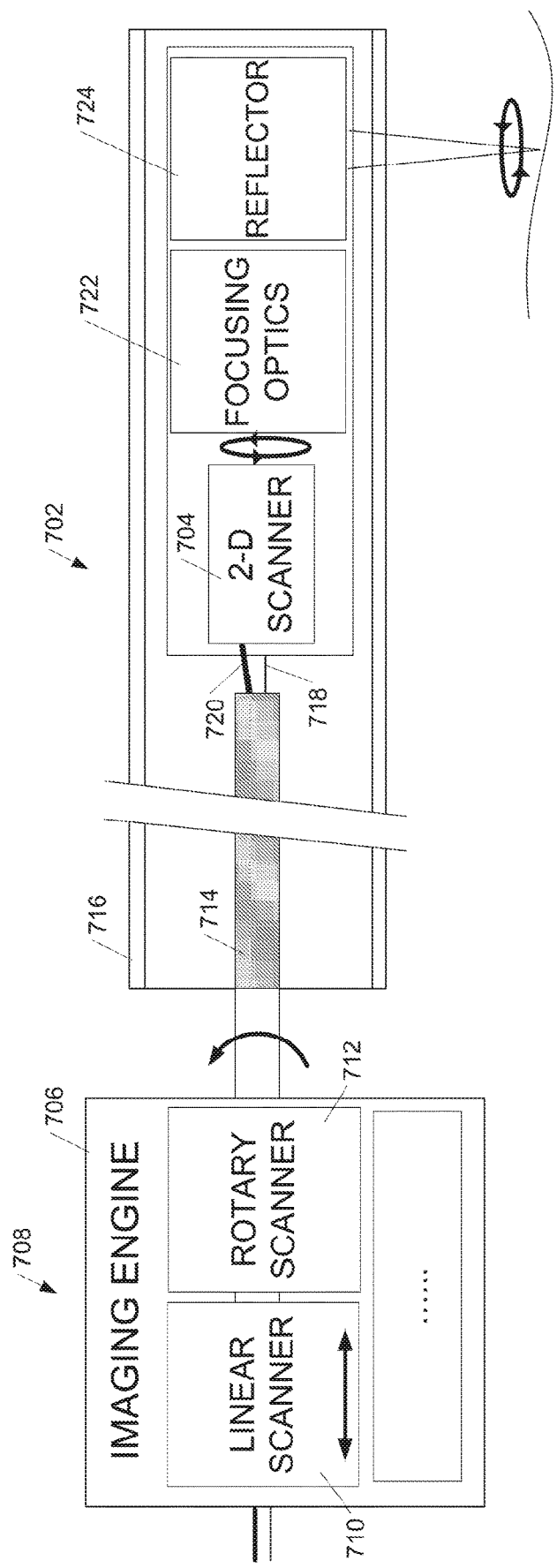
FIG. 7 is a schematic view showing an embodiment in which the distal section comprises a 2-D scanner, and the imaging engine of the proximal section comprises a rotary scanner and/or a linear scanner.

In FIG. 7, the distal section 702 contains a 2-D scanner 704, while the imaging engine 706 of the proximal section 708 contains a linear scanner 710 and/or a rotary scanner 712 that are connected to the distal section 702 by a torque cable 714 or other mechanical cable within the tether or sheath 716. The at least one optical fiber or waveguide 718 and the at least one electrical connection 720 may or may not be contained within the mechanical cable 714. In some embodiments, the 2-D scanner 704 can be substituted by a 2-D optical array. In this embodiment, the slow scanner is located in the proximal section 708, and linearly and/or rotary actuates the distal section 702 including the 2-D scanner 704, focusing optics 722, and reflector 724 via the mechanical cable 714 in order to scan over a 2-D region. In these embodiments, due to the 2-D scanner and reflector being proximally scanned in unison, the 2-D closed curve pattern in the focal plane does not rotate locally, i.e. $Rot(\theta)$ in equation (2) is the identity matrix. If a rotary scanner 712 is used, the imaging engine 706 can also contain a fiber optic rotary junction, which enables optical coupling between the optical waveguide 718 in the tether 716 and the imaging engine 706. This embodiment has the advantage that the distal section 702 has a relatively small diameter and rigid length, which can be desirable for certain applications, but has the possible disadvantage of non-uniform scanning and other imaging artifacts from proximal scanning.

Figure 8A:
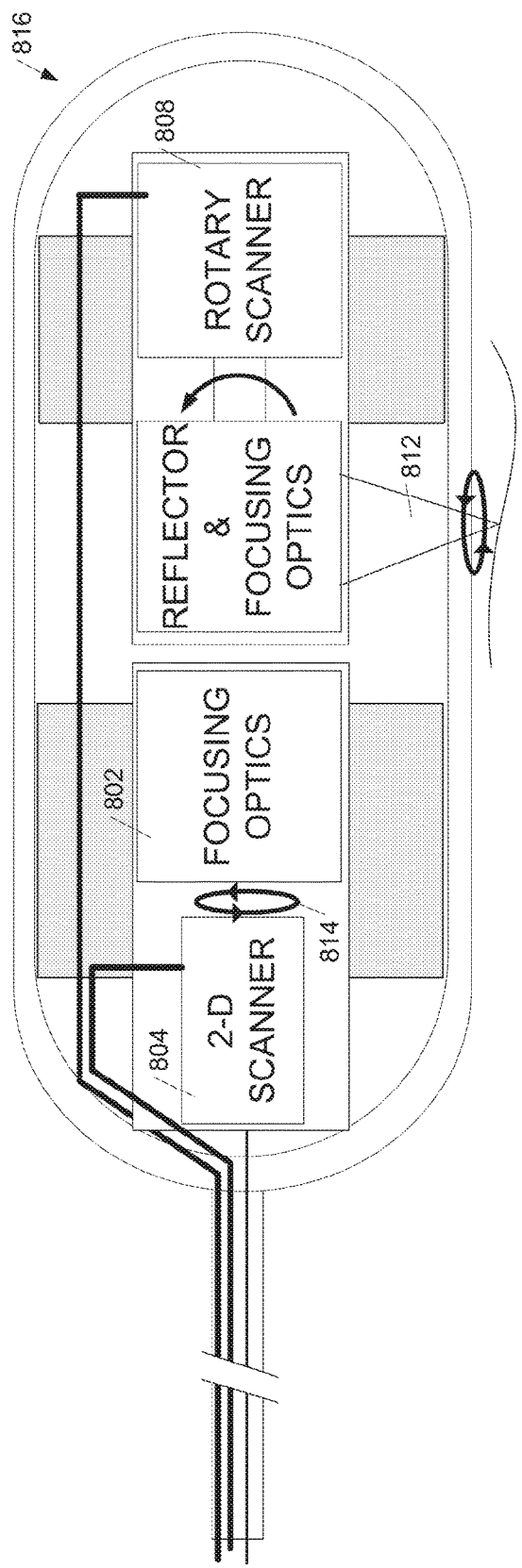
FIG. 8A is a schematic view showing the optical path collimated or weakly focused or weakly diverged by a first set of focusing optics, and the rotary scanner imparting motion to a reflector and second set of focusing optics serving as the imaging objective, which is capable of imaging at high numerical aperture.
Figure 8B:
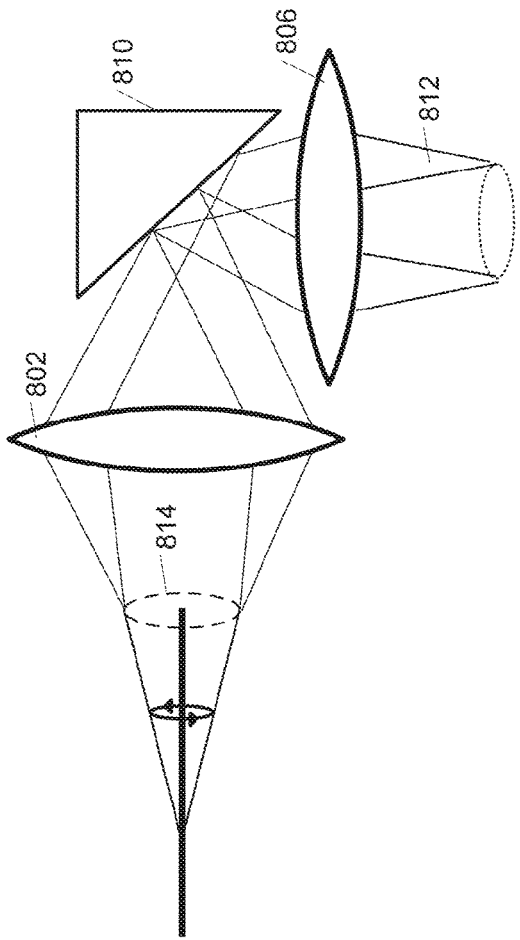
FIG. 8B is a schematic view of an exemplary optical system layout that could be used with the configuration of FIG. 8A, in which a first set of focusing optics placed after the 2-D scanner serves to collimate or weakly focus or weakly diverge light from the 2-D closed curve trajectory produced by the 2-D scanner, and a second set of focusing optics focuses the 2-D closed curve at a short working distance and high numerical aperture.

In FIG. 8, the focusing optics 802 after the 2-D scanner 804 produce an optical beam that is either collimating or weakly focusing or weakly diverging. FIG. 8A shows a schematic of an exemplary embodiment, and FIG. 8B shows an exemplary optical system layout. The beam impinges on a second set of focusing optics 806 that is mounted to the rotary scanner 808, via at least one reflector 810 on the center axis of the rotary scanner 808. The second set of focusing optics 806 produce a focusing beam 812 that has a relatively short working distance to the focal plane and high numerical aperture, serving as an imaging objective. The reflector 810 can be a deformable mirror or a curved mirror, which can reduce optical aberrations and improve the performance of the optical system. In some embodiments, one or both sets of focusing optics and the reflector 810 can be mounted to the rotary scanner 808 for rotation. In some embodiments, one or both sets of focusing optics and the reflector 810 can be part of a single monolithic optical component. Similar to the low numerical aperture embodiment, the reflector 810 directs the 2-D trajectory 814 at substantially 90 degrees or an acute angle forward or backward relative to the longitudinal axis of the distal section 816, such that the focal plane lies at or near to the outer surface. Having the 2-D trajectory at an angular tilt relative to the longitudinal axis results in a tilted focal plane, which can be beneficial for covering a range of imaging depths.

FIG. 9 is a set of embodiments that modifies the function of some of the earlier embodiments. In embodiments that use high numerical aperture focusing, the working distance and depth of field of the optical system is relatively short, which places strict requirements for mechanical tolerances of the assembly and optical alignment. For example, at 500 nm wavelength, numerical aperture of 0.2 and Gaussian waist ($1/e^2$) size of 3 μm in the focal plane, the confocal depth of field is ~30 μm, while standard machining tolerances are about 50-100 μm. Therefore, in embodiments that use high numerical aperture focusing, compact mechanisms for adjusting the position of the focal plane are important. In embodiments that use low numerical aperture focusing, focal plane position adjustment can also be important when imaging is performed in scenarios where the location of the tissue being imaged can shift or vary, such as in large lumens. In FIG. 9A, the focusing optics 902 after the 2-D scanner 904 are mounted on a 1-D linear actuator 906 such as a mechanical, hydraulic, pneumatic, magnetic, piezoelectric, MEMS, shape memory alloy or other actuator that allows the focusing optics to translate along the longitudinal axis of the distal section 908. Translation of the focusing optics 902 in front of the 2-D scanner 904 can have the effect of translating the focal plane of the optical system a short distance 910 further or nearer to the outer surface 912 of the distal section 908. This functionality can compensate for small inaccuracies in mechanical assembly that lead to a de-centration of the central optical path, small variations in the dimensions of the distal section 908, or small variations in the distance of the object being imaged from the distal section 908, such as the wall of an organ lumen. The linear actuator 906 can have a relatively slow response time of the order of the period of the rotary scanner 918, which can adjust for slow changes in the focal plane such as tissue moving in and out of focus, or it can have a faster response time that allows for more rapid correction of focal variations within the circumference caused by mechanical inaccuracies. In FIG. 9B, the 2-D scanner 904 is mounted on the 1-D linear actuator 906, allowing it to translate along the longitudinal axis of the distal section 908 proximal to the focusing optics 902. This similarly has the effect of translating the focal plane of the optical system a short distance 910 further or nearer to the outer surface 912 of the distal section 908. In FIG. 9C, the focusing optics 914 have the ability to vary or adjust their focal position, and are also known as variable focus optics. Examples of variable focus optics 914 are deformable lenses, liquid lenses, or other optics that can have their focal length adjusted by electrical, mechanical or other means. Varying the focus of the optics 914 after the 2-D scanner 904 has the effect of translating the focal plane of the optical system further or nearer to the outer surface 912 of the distal section 908 while not requiring an additional linear actuator. In FIG. 9D, the distal section 908 is split into at least two portions, and the 2-D scanner 904 and the rotary scanner 918 are in separate portions, which are mated by high thread count screw threads 916. The focusing optics 902 after the 2-D scanner 904 is on a separate portion from the 2-D scanner 904, such that the spacing between the 2-D scanner 904 and the optics 902 after it can be precisely adjusted by manual adjustment of the screw mechanism, which has the effect of translating the focal plane of the optical system further or nearer to the outer surface 912 of the distal section 908. Translation based on screw thread can be highly accurate and have longer travel range than some compact 1-D linear actuators, and can be used for setting a single focal position with high precision during the manufacturing process. 100 threads per inch thread count produces 25 microns of travel per screw revolution, and even higher thread counts for higher precision are readily available. In addition, the rotary scanner 918 is centered in the distal section 908 by set screws 920 manually adjustable from the outside, which can be used to precisely adjust centration and tilt of the rotary scanner 918. These manual adjustments may not be conveniently done during real-time imaging, but can overcome mechanical tolerances in setting accurate optical focal position.

Figure 10:
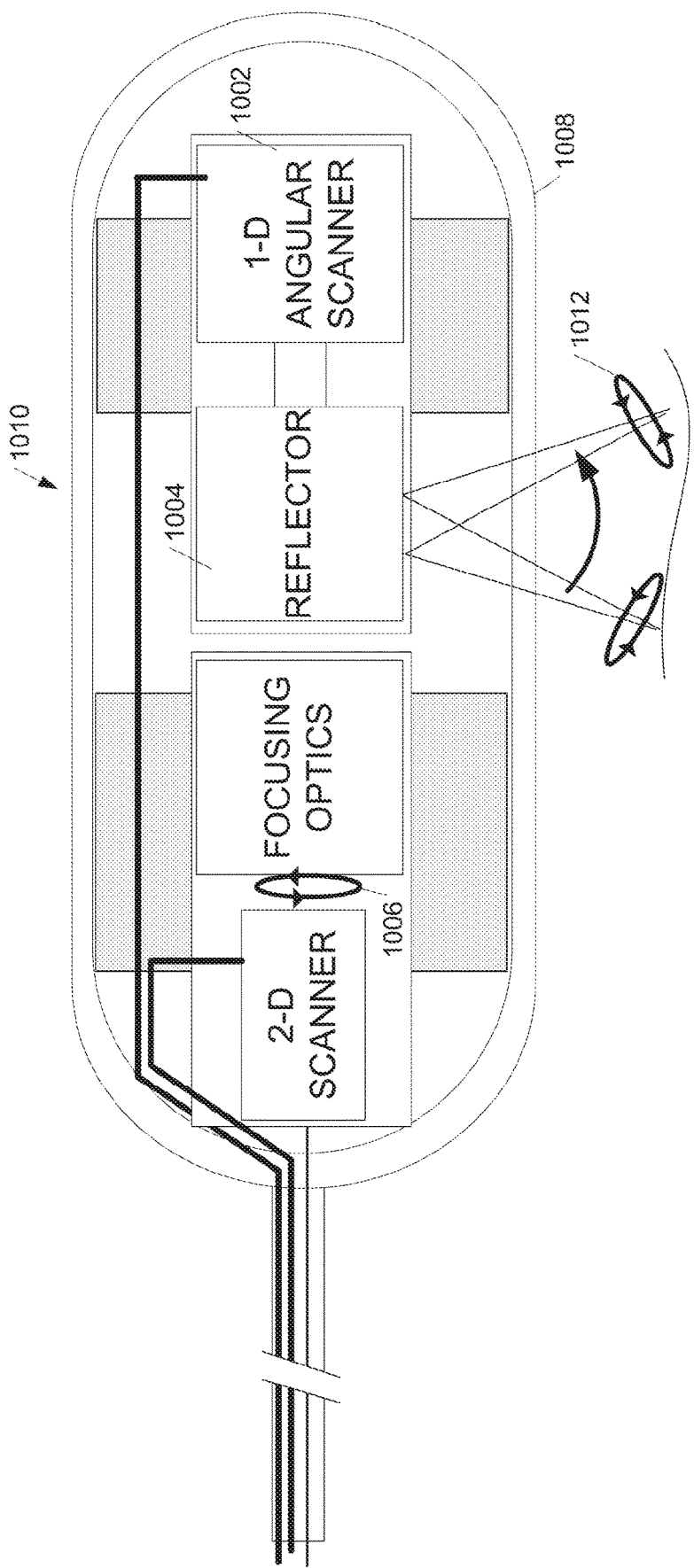
FIG. 10 is a schematic view showing the distal section containing a 2-D scanner and a 1-D angular scanner, where the 1-D angular scanner tilts a reflector over a range of angular deviations covering a limited arc.

FIG. 10 is an embodiment that uses a 1-D angular scanner 1002 to actuate a reflector 1004 for the slow scan. The reflector 1004 directs the 2-D trajectory 1006 at substantially 90 degrees or at an acute angle forward or backward relative to the longitudinal axis, such that the focal plane lies at the outer surface 1008 of the distal section 1010 or a short distance away from the outer surface 1008. The slow scan plane may be in a longitudinal plane (parallel to the page) or a transverse plane (perpendicular to and going into the page). The actuation of the angular scanner over a range of angular deviations results in the 2-D closed curve 1012 in the focal plane tracing out a 2-D strip region covering a limited arc segment.

FIG. 11 shows embodiments in which a 2-D optical array 1102 of fibers or other waveguides or sources deliver light to and receive light from the distal section 1104. A 2-D array 1102 can be used or manipulated to generate a circular or other 2-D optical trajectory. In FIG. 11A, a 2-D scanner or other actuator 1106 at the proximal section 1108 scans laser light in a 2-D trajectory into the 2-D array 1102 at the proximal section 1108 of the device, which has the effect delivering a circular or other 2-D closed curve scan 1110 into the distal section 1104. The advantage of this design is that a 2-D scanner 1106 at the proximal section 1108 can have better performance such as higher precision or speed control, or be lower cost than a compact scanner in the distal section 1104. In FIG. 11B, a portion of the proximal face of the 2-D array 1102 is illuminated with an incoherent light source 1112 such as a light emitting diode, producing a circular or other 2-D optical pattern 1114 in the distal section 1104. The return optical signal can be detected by a 2-D camera sensor 1116 in the proximal section 1108. The advantage of this design is that imaging speeds can be fast due to fast frame rate camera sensors available.

Figure 12:
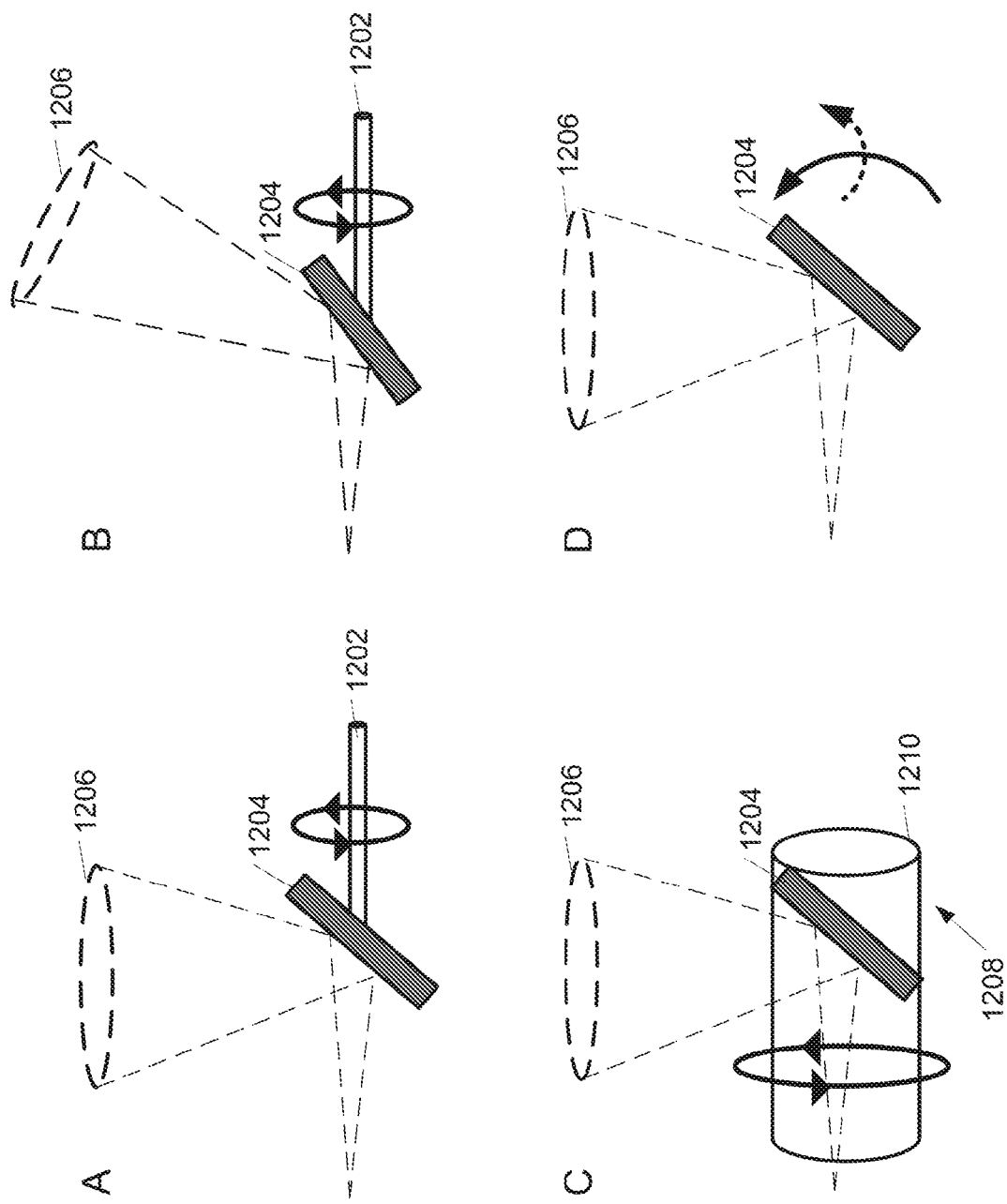
FIG. 12 is a summary of exemplary scan geometries that are possible with the aforementioned embodiments.

FIG. 12 summarizes some exemplary embodiments of scan geometries. The dashed lines indicate the central axis of the optical beam. FIG. 12A shows a rotary scanner 1202 actuating a reflector 1204 that reflects a 2-D closed curve 1206 at a substantially 90 degree angle relative to the longitudinal axis of the distal section. FIG. 12B shows a rotary scanner 1202 actuating a reflector 1204 that reflects a 2-D closed curve 1206 at an acute angle pointing forward (or backward) relative to the longitudinal axis. FIG. 12C shows a rotary scanner 1208 that has a hollow section 1210 along the longitudinal axis, that permits the 2-D closed curve 1206 to be projected via the hollow section 1210 and reflected by a reflector 1204 on the end of the rotary scanner 1208. This embodiment may be advantageous for conserving the longitudinal length of the assembly. FIG. 12D shows a 1-D angular scanner actuating a reflector 1204 over a limited arc in either a longitudinal or transverse plane. In FIGS. 12A-C, the rotation of the rotary scanner can be made to occur over a limited range of rotation angles, thereby performing an equivalent function to an angular scanner.

FIG. 13 shows some schematics of exemplary embodiments of the 2-D optical projector, which is a 2-D scanner or 2-D optical array or other mechanism that projects a 2-D optical pattern. The 2-D scanner can be a piezoelectric, electro-optic, acousto-optic, MEMS, electromagnetic, or other actuator capable of high speed 2-D actuation. FIG. 13A is an exemplary schematic of a piezoelectric actuator (e.g. manufactured by Physik Instrumente), namely a piezoelectric tubular actuator 1302 with 4 quadrant electrodes 1304 and electrical connections 1306 enabling actuation on orthogonal axes. The optical waveguide or fiber 1308 can pass through the center of the actuator 1302 for design compactness, and is mounted or glued to the tip 1310 of the actuator. When the piezoelectric actuator 1302 is actuated, the fiber 1308 behaves as a fixed-free cantilever and can be excited into a resonant state if the excitation frequency is selected appropriately. FIG. 13B is an exemplary schematic of an electro-optic device 1312 with a voltage supply 1314 that can rapidly deflect an optical beam. FIG. 13C is an exemplary schematic of a MEMS actuator 1316 that can deflect an optical fiber 1318 in orthogonal axes. FIG. 13D is an exemplary schematic of an electromagnetic device 1320, namely a coil or solenoid 1322, which can function as a forced oscillator and perturb a bead of magnetic or magnetized material 1324 that is mounted on an optical fiber 1326. When the bead 1324 is positioned off the center axis of the solenoid 1322, the fiber 1326 can be actuated in 2 dimensions (e.g. Min et al., Optics Letters 2011). Other embodiments of electromagnetic or magnetic devices for 2-D actuation are possible. FIG. 13E is an exemplary schematic of the distal end face 1328 of a 2-D optical array 1330, such as a fiber bundle, a multi-core fiber, a fiber fanout, or other array of multiple optical paths. A 2-D array 1330 can be used to generate a 2-D optical trajectory 1332, using a 2-D scanner to scan an optical beam on the end face at the proximal end of the 2-D array, or illuminating a portion of the proximal end face such as but not limited to an annular geometry to produce a 2-D optical pattern 1332 projecting from the distal end face 1328.

Figure 14A:
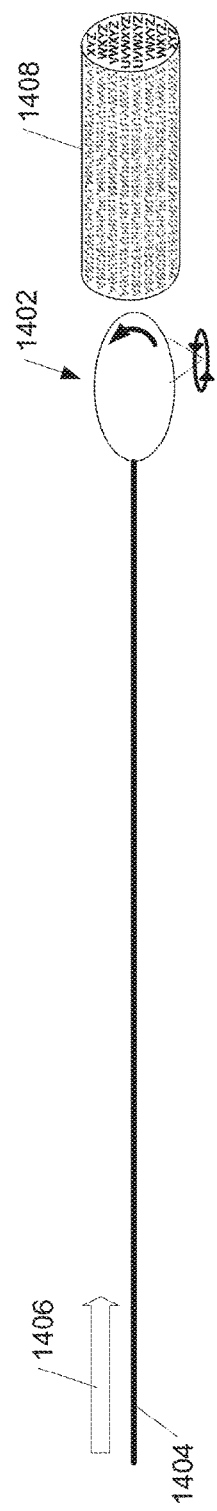
FIG. 14A-B are schematics and exemplary image data showing a proximal scan actuation of the tether producing a mosaic of sequentially acquired images.
Figure 14B:
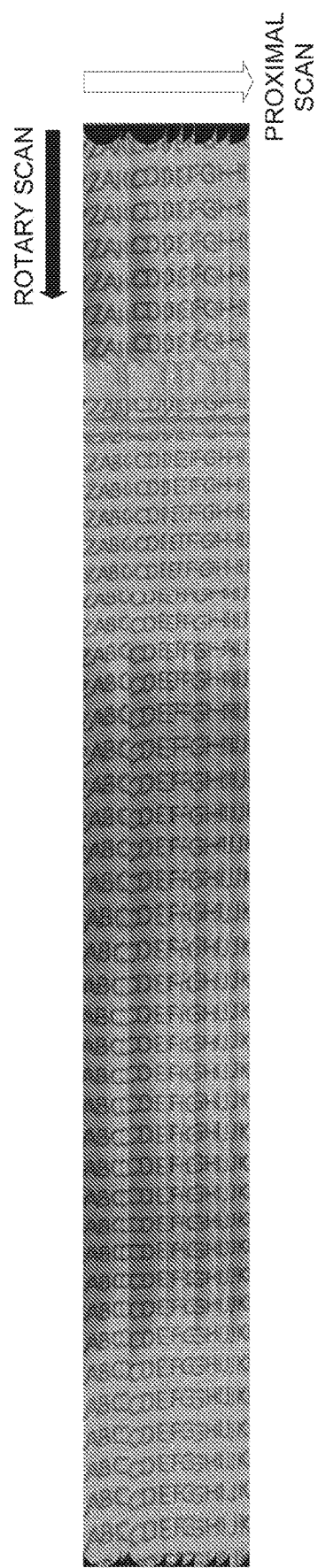

FIG. 14A is a schematic showing the mechanism of proximal actuation on the tether, and FIG. 14B is exemplary en face OCT imaging data that consists of sequential images that are mosaicked to form a larger field of view than an individual 2-D strip. The entire distal section 1402 may be actuated by pulling or pushing on the tether 1404 synchronously or asynchronously to the scanners in the proximal or distal section. This tether actuation 1406 occurs on the tether 1404 near the proximal section, and may be generated by an electrical, mechanical or other linear actuator that is part of the imaging engine, or manually by a clinician or other operator. Performing this tether actuation 1406 during imaging can cover an area that is larger than the 2-D area covered by the cycloid trajectory alone. Sequential images acquired can be mosaicked to give a larger field of view. In the illustrative example of FIG. 14B, sequential images were acquired from a rolled-up piece of paper printed with an alphabet grid 1408, and the proximal actuation 1406 of the distal section 1402 through the paper roll 1408 enabled coverage of the longitudinal extent of the paper roll 1408, which is longer than the width of the cycloid trajectory alone. Given the potential inaccuracy of proximal actuation 1406 for controlling the translation speed of the distal section 1402, the speed of this tether actuation 1406 can be approximately calculated as half the 2-D strip width multiplied by the frequency of the slow rotary or angular actuator $f_{slow}$, which ensures some overlap of each 2-D strip to facilitate mosaicking. The advantage of this imaging method is that the cycloid scanning enables accurate visualization of en face image features, while the proximal tether actuation enables a large field of view.

Figure 15:
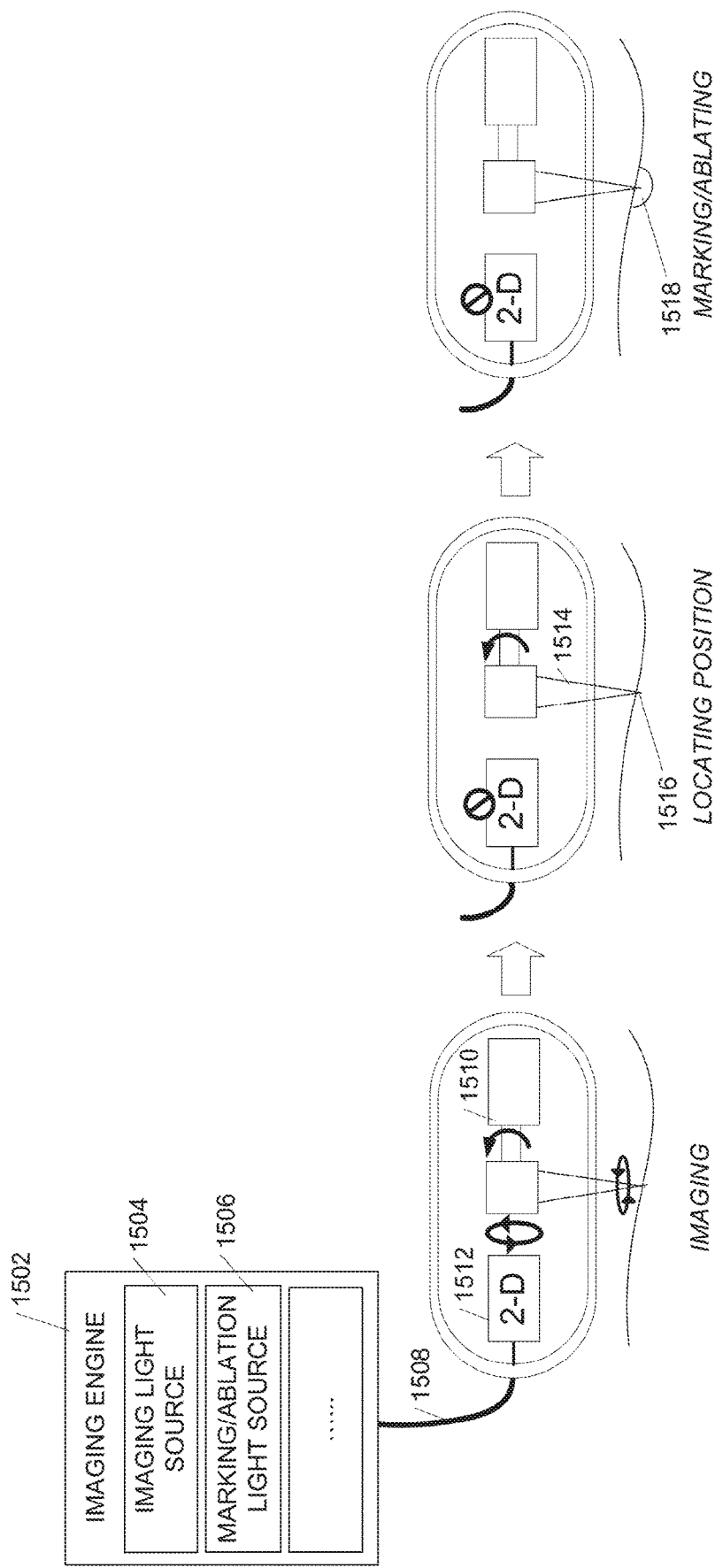
FIG. 15 is a schematic view showing an exemplary embodiment of the device being used to perform laser marking or ablation over a region of interest, guided by imaging.
Figure 16A:
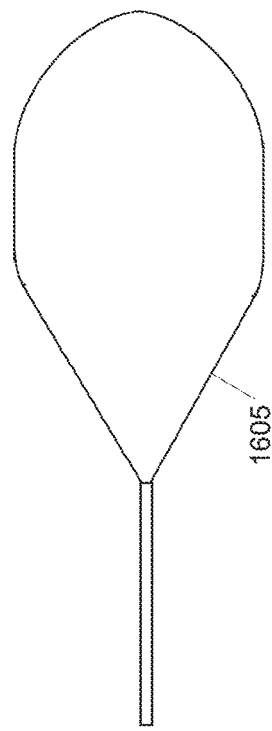
FIG. 16A is a schematic showing an embodiment of the distal section in which one end has a tapered conical shape to facilitate retrieval of the device.
Figure 16B:
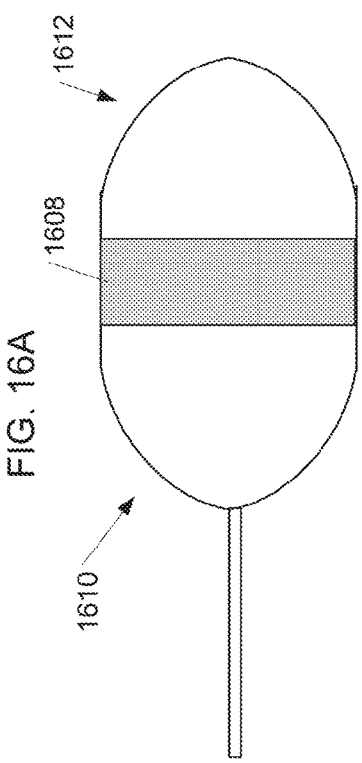
FIG. 16B is a schematic showing an embodiment of the distal section in which the two ends are made of a different material that is less transparent and has an enhanced functional property such as lubricity or other function compared to the central portion.
Figure 16C:
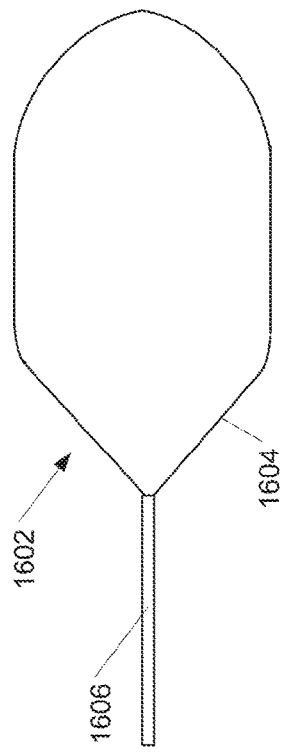
FIG. 16C-D are schematics showing an embodiment of the distal section in which the two ends are of a larger or smaller diameter compared to the central portion.
Figure 16D:
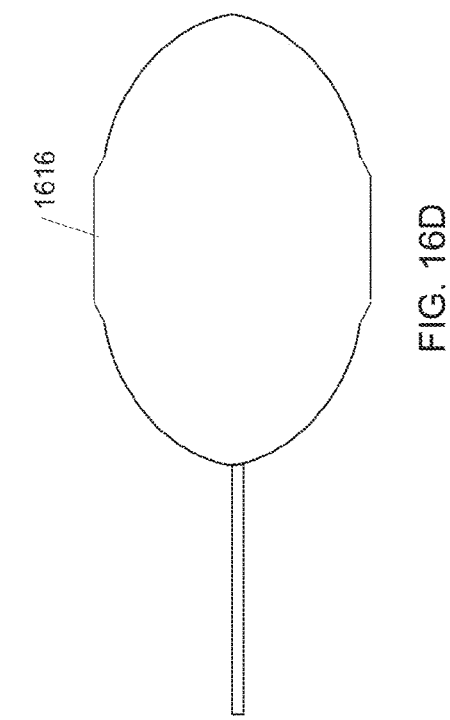

FIG. 15 shows a schematic of the device set up to perform imaging and laser marking or treatment. When a region of interest is noted on the 2-D strip images that are acquired by the device, it can be desired to place thermal, ablative or other light-induced superficial damage on the tissue region by means of a laser or other light source of wavelength differing from the wavelength used for imaging, for purposes of marking or treatment. The imaging engine 1502 has at least two light sources of differing wavelengths, at least one of which is for imaging 1504 and at least one is for ablation 1506. The tether 1508 contains at least one optical fiber that is either transmissive at the at least two wavelengths, or has more than one aperture transmitting the at least two wavelengths through separate apertures such as a dual clad fiber or multi-core fiber. Based on initial imaging using the at least one imaging wavelength, one or more locations on the circumference or other slow actuating dimension of the rotary or angular scanner 1510 is selected for laser marking or treatment. The 2-D scanner 1512 is then made to cease operation or scan a very small range in one or two dimensions, such that the device is scanning substantially in a single slow axis due to the rotary or angular scanner 1510. Thereafter, in some embodiments, the rotary or angular scanner 1510 is made to cease or slow down motion in order to position the optical beam 1514 at the desired marking or treatment location 1516, and the output wavelength switched to the at least one marking or treatment light source 1506, for the marking or treatment 1518 to proceed. The rotary or angular scanner 1510 is selected for accurate motion at relatively low speeds, therefore rapid deceleration or acceleration for the marking or treatment, preceded by image guidance or followed by resumption of imaging is feasible. In other related embodiments, the rotary or angular scanner 1510 could be allowed to continue rotation during ablation, while a fast optical shutter is used in the imaging engine 1502 to enable the ablation light source 1506 output while the optical beam 1514 is momentarily positioned over the desired ablation location 1516. Similarly, the use of a low speed rotary or angular scanner 1510 for the optical beam 1514 positioning can be advantageous, because the optical shutter will not require an excessively rapid response time to perform a controlled optical exposure for the marking or ablation process 1518.

FIG. 16 is a schematic of some exemplary embodiments of the distal section. The distal section can be shaped or otherwise mechanically designed to improve the function and performance of the device. FIG. 16A shows one end 1602 of the distal section with a 45 degree 1604 or less than 45 degree 1605 conical taper. This can be advantageous when the distal section is retracted via the tether 1606 and passed through constrained orifices such as but not limited to muscular sphincters, in which the conical taper can improve ease of retraction or retrieval. FIG. 16B shows the distal section produced out of at least two materials, where the central portion 1608 of the distal section for imaging is a transparent material, and the two ends 1610 and 1612 are made out of less transparent materials but optimized for other purposes such as but not limited to lubricity, hydrophobicity, hydrophilicity, elasticity, porosity or other functional properties excluding optical transparency. FIG. 16C-D show the distal section where the central portion has a different diameter from the two ends. The central portion 1614 can be a smaller diameter than the two ends in FIG. 16C, to reduce compression of tissue at the imaging area. The central portion 1616 can also be a larger diameter than the two ends in FIG. 16D, to improve tissue contact at the imaging area.

The disclosure also describes methods for accurate reconstruction of an image from the cycloid scan. Compared to a raster scan, the cycloid scan has a more complex trajectory, such that specific details of implementation are required in order to reconstruct an accurate image. These methods relate to electronic synchronization and control of hardware such as data acquisition, scanner control, and focus adjustment, as well as reconstruction algorithm methods. Without careful attention to these details, the acquired images may have errors/distortions that are difficult to correct.

Figure 17:
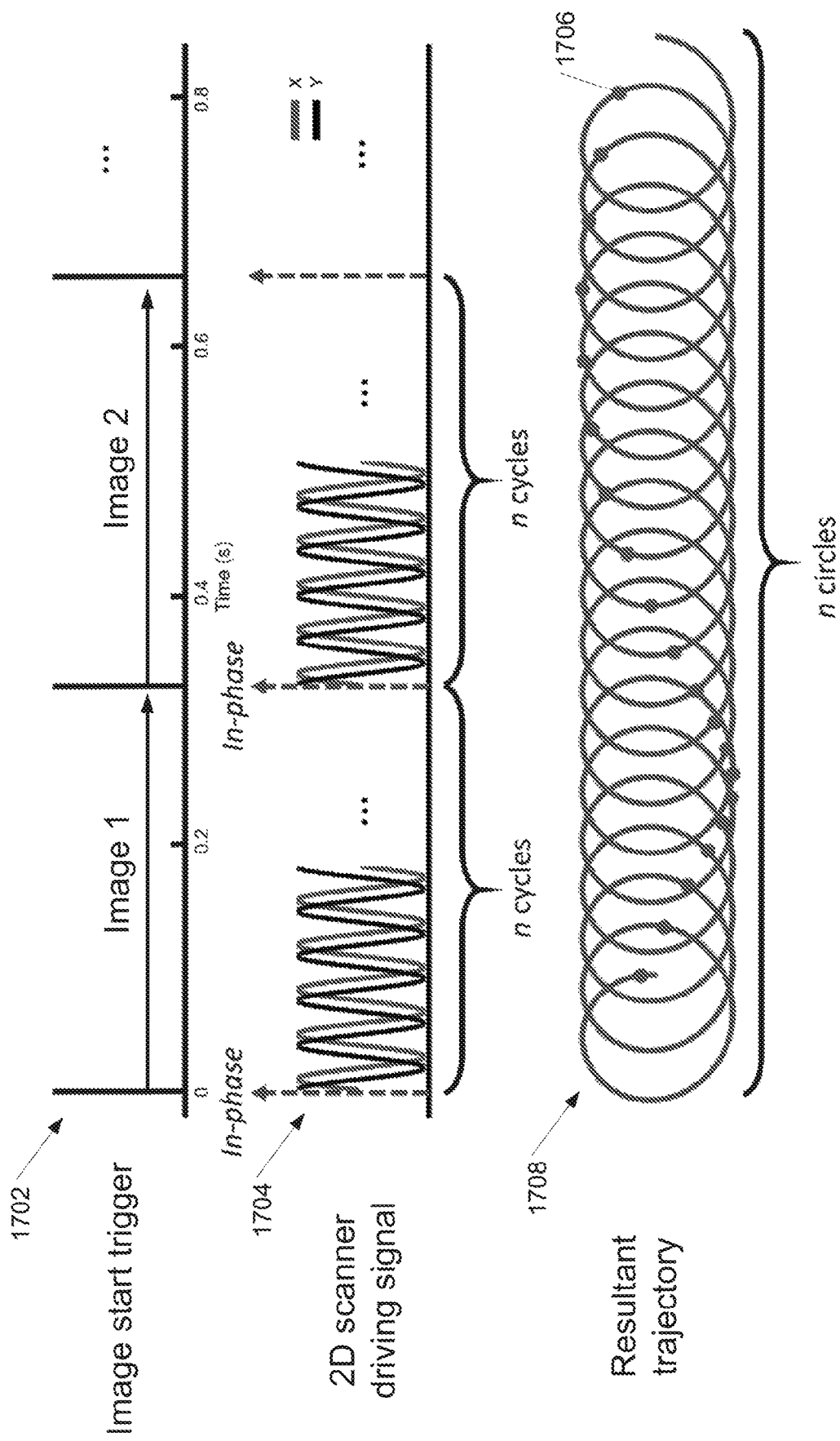
FIG. 17 is a schematic showing one embodiment of a method to control the scanning and acquisition, wherein the 2-D scanner is synchronized to data acquisition.

The device contains multiple scanners/actuators, so it is important that they are controlled and synchronized in a fashion that delivers repeatable performance while not being overcomplicated. In one possible embodiment, an electronic controller is used to generate electronic signals that control the actuators, while data acquisition hardware and a processor acquires and processes signals from an imaging system. The hardware that generate signals (controllers) and the hardware that acquire signals may be part of the same device such as a combined D/A signal generator and A/D data acquisition board, or they may be separate devices. The controllers and data acquisition hardware should share a master timing clock so they can be synchronized with minimal timing error. FIG. 17 is a schematic showing one embodiment of synchronization. In this embodiment, image acquisition is synchronized to a start trigger waveform 1702, which is in turn synchronized to a pair of quadrature sinusoidal waveforms 1704 or other waveforms that drive the 2-D scanner. The points 1706 on the cycloid trajectory 1708 are exemplary points equally spaced by the temporal period (or a multiple) of the waveforms 1704, and are shown to have a slow rotation about the center of the circular trajectory due to the reflector inversion phenomenon (see equation 2). Timing/phase errors between the acquisition start and the phase of the waveforms driving the 2-D scanner will manifest as an error in the reconstruction phase term (see equation 3), leading to image distortion when reconstructed that is difficult to systematically correct. Therefore it is imperative that synchronization between acquisition and the 2-D scanner drive waveforms have as minimal timing/phase error as possible. It is possible, but not required that the slow rotary or angular scanner be also electronically synchronized to the 2-D scanner. In a related embodiment, the controller or controllers generate waveforms sharing the same timing clock that drive not only the 2-D scanner but also the rotary or angular scanner, such that both scanner are synchronized. This is possible if the waveform generating hardware that is synchronized to data acquisition has multiple analog or digital outputs. In this configuration, the rotary or angular scanner can be synchronized such that it always starts at the same angular position relative to the start of each image. This is further expedited if the rotary or angular scanner has a position encoder and/or closed loop control such as a servomotor or galvanometric scanner. In order to reconstruct an arbitrary image, a grid target (such as a grid printed on paper) can first be imaged, and the correct phase term φ determined empirically that generates the most accurate grid image. This phase term is related to the relative orientation of the 2-D scanner and the rotary or angular scanner, which is fixed during device assembly. As long as the rotary or angular scanner always begins to rotate from the same starting position, the value of $\phi$ used for reconstruction will not need to be changed. In another related embodiment, the rotary scanner is controlled by separate hardware that is electronically asynchronous to the 2-D scanner drive waveforms. This embodiment can be preferred if the rotary scanner is accompanied by vendor-designed hardware intended for optimal scan performance but cannot be externally synchronized, and/or the waveform generating hardware that is synchronized to data acquisition has an insufficient number of signal outputs. In this embodiment, only the 2-D scanner is synchronized to the acquisition, and the rotary scanner may start at any arbitrary rotary position.

Figure 18A:
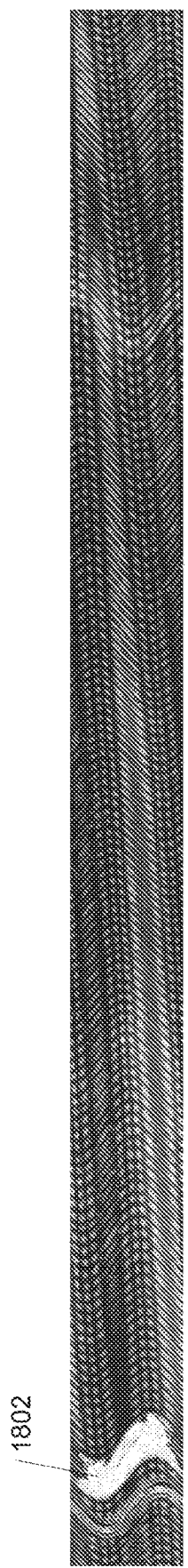
FIG. 18A is an exemplary raw image obtained with an embodiment of the device, that has not yet been reconstructed to give a geometrically accurate image.
Figure 18B:
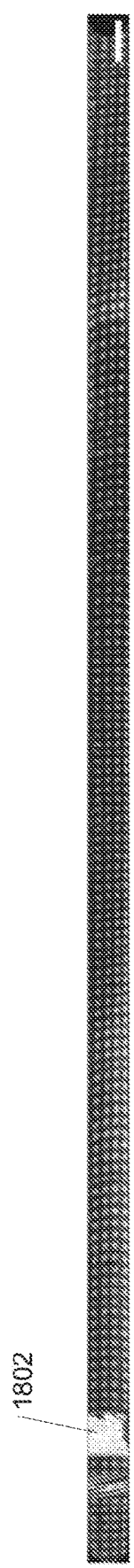
FIG. 18B is an exemplary image obtained with an embodiment of the device, that has been accurately reconstructed, and showing a fiducial marker that is part of a method for reconstructing an image.

FIG. 18A shows an exemplary image that is an en face OCT image acquired by the device, but is in a 'raw' state that has not yet been correctly reconstructed. There is at least one fiducial landmark 1802 in the image that is generated by a strut or other reflective or scattering or fluorescent feature that is located inside the distal section, and is stationary relative to the outer surface of the distal section. The fiducial landmarks 1802 are important for providing a relative measure of angular position of the rotary or angular scanner, and for evaluating accuracy of reconstruction. In one embodiment of a possible calibration step, the phase term $\phi$ can be determined empirically for some starting angular position of the rotary or angular scanner, based on imaging of a grid target or simply the fiducial landmark 1802. For subsequent images in which the rotary or angular scanner has been arbitrarily restarted from a different angular position, $\phi$ can be estimated by identifying the location of the fiducial landmark 1802 and measuring how much it may have moved along the horizontal (slow) axis in the image relative to the calibration position. FIG. 18B shows the image in FIG. 18A correctly reconstructed, showing the fiducial landmark 1802 preserving its position but now undistorted.

Figure 19:
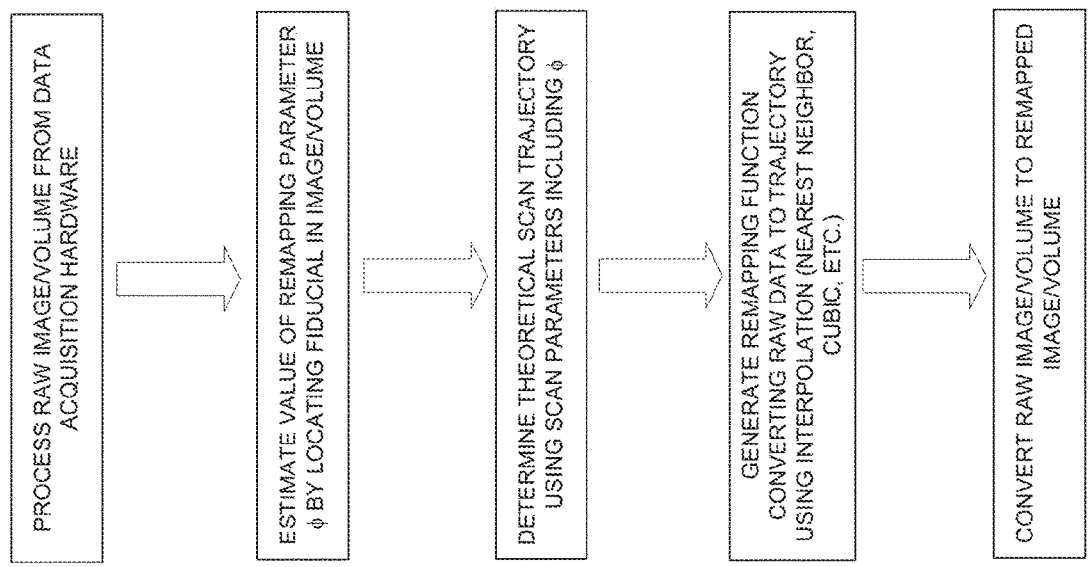
FIG. 19 is a flowchart showing an exemplary reconstruction algorithm for reconstructing raw images.

FIG. 19 is an outline of an embodiment of a reconstruction algorithm for converting a raw image to a correctly reconstructed image. After the raw image is generated, the fiducial and its location on the horizontal axis is identified, giving an estimate of the phase term $\phi$. Thereafter, the complete mathematical description of the theoretical scan trajectory can be determined analytically. This is used to generate a remapping function that remaps the raw image to the correct trajectory using nearest neighbor interpolation, cubic interpolation, or other mathematical interpolation method. The remapping function is then used to convert the raw image to the correct reconstruction.

The nature of the 2-D closed curve scan is such that it produces a rescanning effect, i.e. it scans over a region that was already scanned earlier during the slow rotary or angular scan because it is 2-D rather than a 1-D line. If the 2-D closed curve generated by the 2-D scanner is not perfectly symmetric or if the focused spot resolution of the 2-D closed curve scan varies slightly within the scan, reconstruction assuming the analytical trajectory including the rescans may produce image distortions. Due to manufacturing imperfections or environmental or other temporal fluctuations, the 2-D scanner may not consistently produce a perfectly symmetric scan obeying the analytical trajectory throughout the entire slow rotary or angular scan. Due to manufacturing imperfections, optical design limitations or other mechanical inaccuracies, the optical focus may vary within the 2-D closed curve scan such that a rescan may have a different focused spot resolution than the earlier scan.

Figure 20:
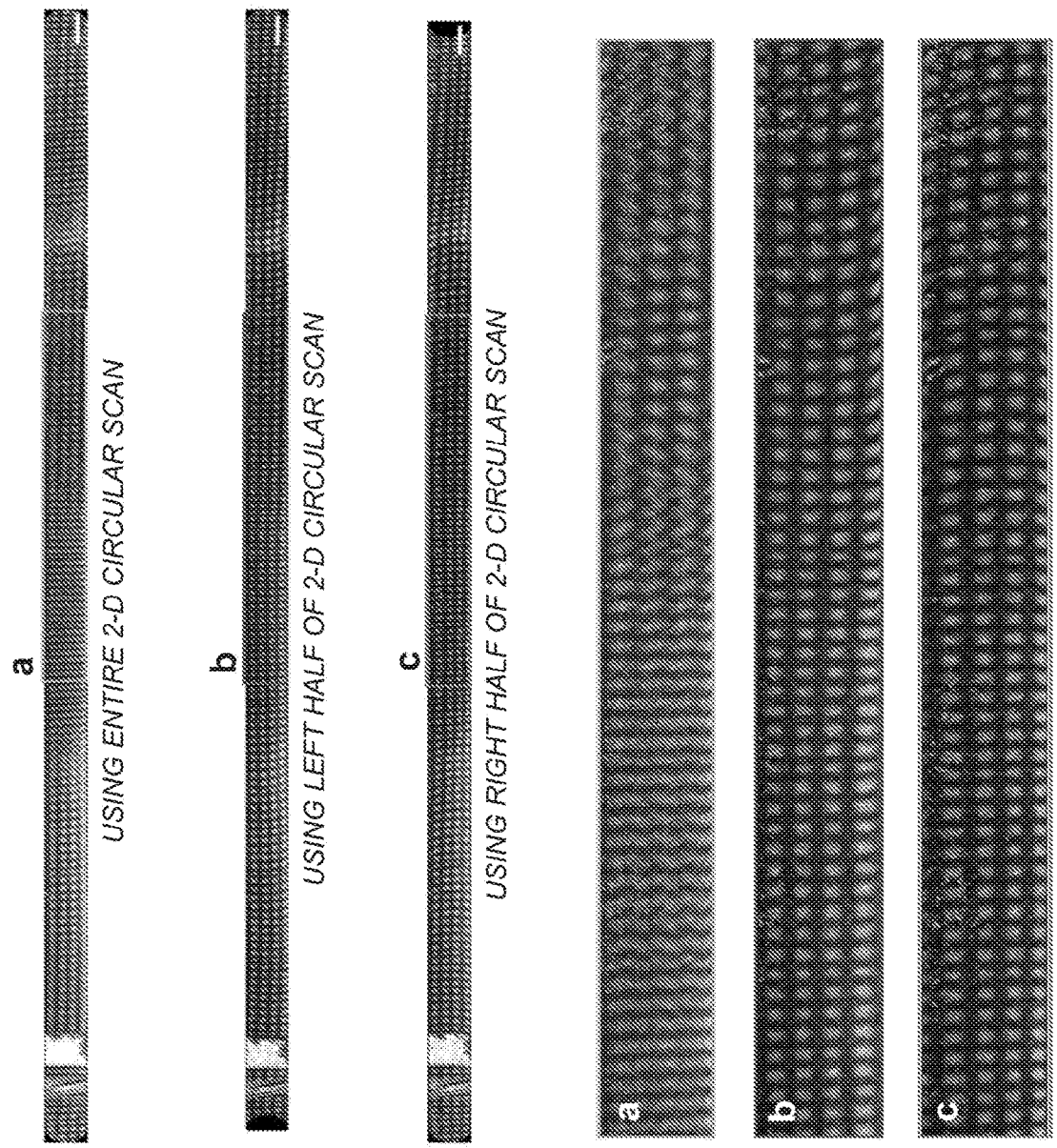
FIG. 20 are exemplary images demonstrating embodiments of the reconstruction algorithm that can minimize distortion artifacts.

In some embodiments, the 2-D closed curve that is generated can be measured frequently by a 2-D position sensitive detector for a calibration step, which gives the true trajectory for reconstruction. However, this neglects the possibility of the trajectory continuing to fluctuate, or variations in focused spot resolution. In other embodiments that can be preferred, only a portion of imaging information from the 2-D closed curve scan is used for reconstruction. In the case of the 2-D closed curve scan being a circular scan, some embodiments for reconstruction use only half of the scan i.e. a semicircular line scan for reconstruction. This is implemented when generating the remapping function for reconstruction, such that only a portion of the raw data is used to generate the remapped output image. In these embodiments, image distortions resulting from an imperfect 2-D closed curve scan can be greatly suppressed. In FIG. 20, exemplary en face OCT images in which image distortions result from using the entire 2-D scan can be nearly eliminated by using one or the other half of the scan. In other embodiments, the separate images obtained from using one and other portions of the 2-D closed curve scan may be separately dewarped, and then recombined to produce a possibly higher quality image that benefits from higher scan density enabled by the rescanning. In yet other embodiments, the light source could be temporally switched or modulated in intensity, wavelength or other parameter between each half of the 2-D closed curve scan, such that the two halves of the scan could be used to generate two separate images obtained with different imaging modalities, imaging contrast or set of imaging parameters.

FIG. 21 shows embodiments that use a linear actuator for focus adjustment of the optical system. In some embodiments, the linear actuator 2102 is electronically synchronous to the rotary or angular scanner 2104. Due to mechanical inaccuracies during assembly or manufacturing that affect optical alignment, it can be necessary to adjust the focal plane of the optical system at different rotary or angular positions on the circumference. In a possible calibration step, the required focal shifts can be measured and used to generate a preset trajectory for the linear actuator. During imaging, such as in FIG. 21A, the linear actuator 2102 moves rapidly and adjusts the optical focus based on the instantaneous position of the rotary or angular scanner 2104. In another related embodiment, the linear actuator 2102 is electronically synchronous to the location of the tissue 2106 or sample being imaged relative to the distal section 2108. During imaging, the location of the tissue 2106 may shift due to physiological motion, or the tissue 2106 may be further or nearer from the distal section 2108 than the default focal position due to the size of the organ lumen, resulting in the tissue 2106 being out of focus. In some embodiments, the location of the tissue 2106 can be tracked in real-time using OCT or other depth sensing modality, and used for adjusting the position of the linear actuator 2102 in real-time such that the focal plane is set to the location of the tissue 2106. In other embodiments, features of the acquired image such as signal intensity or image sharpness can be rapidly analyzed to assess if the focal plane is set adequately to the location of the tissue 2106. During imaging, such as in FIG. 21B, the linear actuator 2102 moves rapidly and adjusts the optical focus based on the instantaneous location of the tissue 2106 being imaged or based on features of the images acquired.

Figure 22:
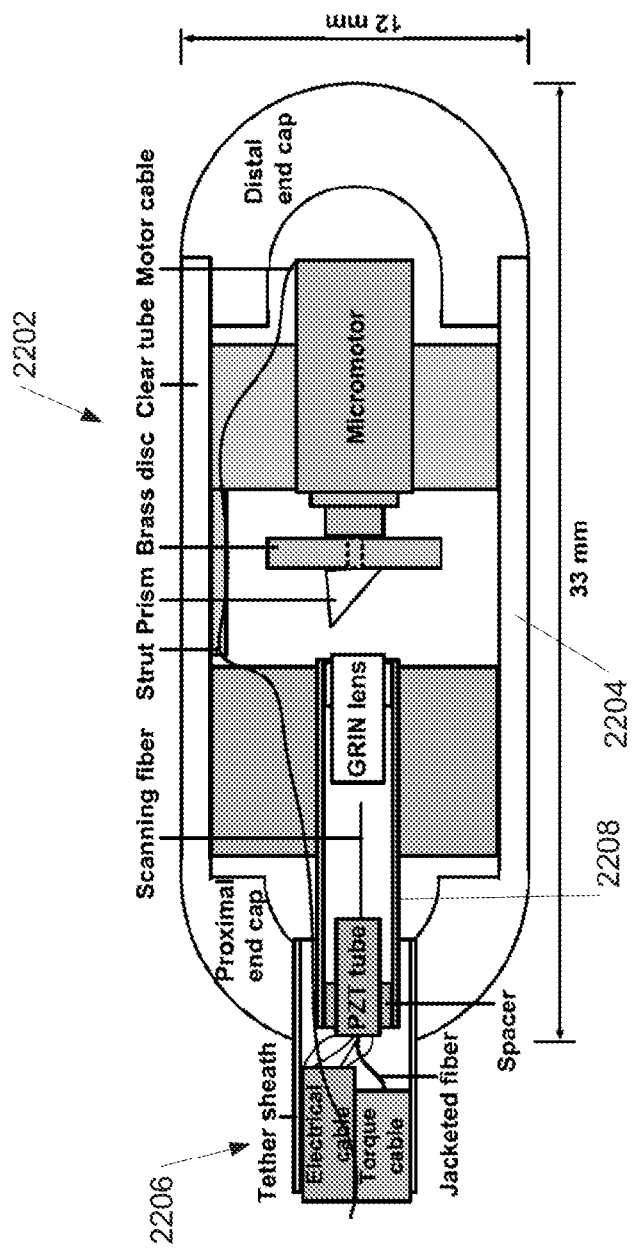
FIG. 22 is a schematic of an exemplification of a particular embodiment of the device.

FIG. 22 is a detailed schematic depicting an embodiment of the present disclosure. A schematic of this particular embodiment was described in FIGS. 4A and 5. In this exemplification, the distal section 2202 has a transparent portion 2204, and its diameter is significantly larger than the tether 2206. The 2-D scanner is a piezoelectric tubular actuator (labelled 'PZT tube') that was described in FIG. 13A, which actuates an optical fiber that is mounted to its tip. In front of the fiber tip is a focusing optic, which is a gradient index (GRIN) lens. The piezoelectric actuator and the gradient index lens are housed in a hypodermic tube 2208. The rotary scanner is an electrical micromotor, which rotates a 45 degree angled prism that is slightly tilted to minimize specular reflections from the inner and outer surfaces of the distal section 2202. The piezoelectric actuator actuates the optical fiber in a circular path, which is reflected and rotated by the micromotor around the circumference, tracing out a cycloid trajectory.

The device uses at least one 2-D optical projector that rapidly projects a 2-D closed curve optical pattern. The 2-D closed curve typically has a relatively small diameter or size. In the preferred embodiment where the 2-D projector is a piezoelectric quadrupole tubular actuator that generates physical deflection of an optical fiber at the mechanical resonance frequency of the optical fiber, the optical fiber tip typically generates a circular diameter in the range of but not limited to 0.5-2 mm. This 2-D closed curve of relatively small diameter can be generated by the 2-D projector at typical speeds of more than 1 kHz (periods/sec) and preferably more than 2 kHz. Therefore the 2-D projector is capable of high speed 2-D actuation, which is preferred to occur at the distal end of the device for optimal speed and precision.

The device also uses at least one scanner that performs rotary or angular scanning. The rotary or angular scanner rotates a reflector that reflects the 2-D closed curve from the 2-D projector at an angle that is substantially 90 degrees relative to the longitudinal center axis of the device, or at a substantially large acute angle relative to the longitudinal center axis of the device. The rotary scanner scans the 2-D closed curve around the circumference of the device, which is typically a large scan length relative to the 2-D closed curve. The rotary scanner is preferred to be an electric rotary motor actuator located at the distal end of the device for optimal rotary precision. For a device of about 3 mm diameter such as a catheter probe, the rotary scanner scans a length that is larger than about 10 mm, the device circumference. For a device of about 12 mm diameter such as a capsule, the rotary scanner scans a length that is larger than 40 mm. Therefore the rotary scanner scans a length at the device circumference that is in the range of but not limited to 5-80 times larger, and preferably at least 10 times larger, than the diameter of the 2-D closed curve at the fiber tip of the 2-D projector. The large scan length covered by the rotary scanner is covered at a much slower speed than the 2-D projector covering a small scan length. For a 2-D projector speed of 2 kHz and an optical focused spot size of 20 µm or less, the rotary scan speed is about 2 Hz (revolutions/sec) for a 3 mm diameter device and less than 1 Hz for a 12 mm diameter device. For higher resolution microscopy imaging at smaller optical spot sizes of about 2 µm, the rotary scan speed is about 0.2 Hz for a 3 mm diameter device and less than 0.1 Hz for a 12 mm diameter device. Therefore the 2-D projector speed (frequency) is typically but not limited to 1000-10,000 times faster than the rotary scan speed (frequency). The combination of the 2-D closed curve scan and the rotary scan is referred to as a cycloid scan, or more specifically a prolate cycloid in view of the loops. The advantage of combining a rapid 2-D projector speed and a slow rotary scan speed is that the 2-D projector can rapidly acquire local portions of the image with minimal motion artifacts, while the rotary scanner covers a large field of view.

In embodiments that use a rotary scanner, the rotary scanner can be a stepper motor that rapidly performs a series of small discrete angular rotations known as micro-steps to achieve continuous rotation, or a motor that is configured or driven to rapidly rotate in a series of small discrete angular rotations. It can be desirable in some imaging applications for multiple 2-D closed curve scans to be repeated at a particular angular position of the rotary scanner, before the rotary scanner rotates by a discrete angular quantity to the next angular position. In some imaging applications such as optical coherence tomography (OCT) angiography, multiple sequential periodic scans acquired at the same location can be compared to obtain imaging contrast from blood or other flow motion. Therefore multiple sequential 2-D closed curve scans acquired at a particular angular position of the rotary scanner can be used to obtain motion contrast data, which can be built up from multiple angular positions over the entire rotary scanner period to obtain an image showing motion contrast.

In embodiments that use a piezoelectric quadrupole tubular actuator with a resonantly scanning optical fiber as the 2-D projector, more than one resonance frequency of the resonantly scanning fiber may be used. In some imaging applications, more than one imaging modality can be used, such that different types of imaging data can be acquired with the same device, for example using different optical excitation wavelengths or different detection schemes that have different sampling densities or acquisition speeds. The resonantly scanning fiber has an infinite number of allowable resonance frequencies that can be mathematically derived from physical parameters of the fiber cantilever. Therefore in applications where two or more imaging modalities are used, the optical fiber may be excited at two or more resonant frequencies in sequence, which has the advantage of enabling multiple types of imaging that occur at different speeds.

The 2-D closed curve can have a limited size, and there can be applications where a larger scan range from the 2-D projector can be desired, in order to generate a larger field of view. Some embodiments of the 2-D projector can use more than one 2-D scanner or 2-D array in parallel, such as more than one piezoelectric tubular actuator adjacent to each other, to project more than one 2-D closed curve towards the reflector on the rotary or angular actuator, such that the effect of a composite 2-D closed curve with an enlarged major axis length is projected.

There can be embodiments of the device that use a 2-D projector, and rely on a manual operator to translate the device over areas of interest to acquire images. In these embodiments, the manual motion translates the 2-D closed curve scan to generate an image. The advantage of the 2-D closed curve is that the manual motion can occur in any direction that is convenient to the operator to acquire an image. The device may contain a motion tracking mechanism such as an electromagnetic sensor or accelerometer that provides information on the manual motion in order to facilitate image reconstruction.

The image generated by the device is oriented around the circumference of the device, therefore it has a substantially tubular or conical geometry, of which the width is the diameter of the 2-D closed curve scan, and the circumferential length is the scan length of the rotary scanner. The image can be reconstructed or assessed by unfolding the image plane to a flat plane, such that the circumferential length of the image is laid flat. In the unfolded plane, the image is formed by the 2-D closed curve scan being translated in a substantially 1-D axis, i.e. a substantially straight line. Due to the rotary scan length, at the outer surface of the transparent portion of the distal section, being in the range of but not limited to 5-80 times and preferably at least 10 times larger than the diameter of the 2-D closed curve scan the unfolded image has a length many times longer than its width, and is typically a long and narrow strip image. The raw (pre-reconstructed) image data points are acquired over the course of the cycloid scan and follow the cycloid scan trajectory. The image is reconstructed by computing the locations of each raw image data point in the Cartesian coordinate system based on the cycloid scan trajectory (equation 3), and mapping each data point to its Cartesian location. This mathematical operation is referred to as a remapping function. In practice, each raw image data point is mapped to the nearest point in a Cartesian grid of pixel dimensions that approximate or exceed the sampling resolution of the imaging system. The quality of the reconstructed image can be further improved by using interpolation techniques to obtain image pixel values at locations in the Cartesian grid that do not occur exactly at the locations of the raw image data points from the scan trajectory.

The scan trajectory of the device has a unique property such that the 2-D closed curve is rotated slowly about its own center while translated around the device circumference, due to the mirror reflection from the rotary actuator. The rotational orientation of the 2-D closed curve scan at any given time point is dependent on the angular position of the rotary actuator at that time point. The direction of rotation of the 2-D closed curve is dependent on the direction of the rotation of the rotary actuator. The cycloid scan trajectory equation (equation 3) incorporates the effect of this rotation of the 2-D closed curve scan on the trajectory. In some applications where the acquired images may be subject to motion artifacts due to motion from the subject being imaged or physical perturbation of the device by its surroundings, it can be desirable to rotate the rotary actuator alternately in either direction during imaging, to sequentially acquire two or more versions of the same image. Rotating the rotary actuator in alternate directions also rotates the 2-D closed curve scan in alternate directions. Alternating the directions of the scanning in sequential images can have the advantageous effect of capturing images with reduced artifacts from motion that have a specific physical direction. The multiple versions of the image can then be compared or combined using motion correction algorithms to produce an image with reduced motion artifacts.

What is claimed is:

1. An apparatus for scanning a beam on a luminal organ or surgical cavity which comprises:
   a proximal section;
   a tether that connects a distal section to the proximal section; and
   the distal section comprising:
   a transparent portion;
   a two-dimensional (2-D) optical projector that projects an optical beam in a 2-D closed curve optical pattern;
   focusing optics that receives the projected optical beam in the 2-D closed curve optical pattern and directs and focuses the beam; and
   a reflective rotary or angular scanner that scans the projected optical beam focused by the focusing optics from within the distal section through the transparent portion, the optical projector, focusing optics, and reflective scanner operating on the projected beam in series within the distal section prior to projection of the projected beam from within the distal section through the transparent portion toward the luminal organ or surgical cavity.

2. The apparatus of claim 1, wherein the 2-D optical projector is a serial projector that is configured to perform rapid beam scanning in a 2-D closed curve.

3. The apparatus of claim 2, wherein the serial projector performs rapid beam scanning at speeds exceeding 1 kHz.

4. The apparatus of claim 3, wherein the serial projector is a piezoelectrically actuated optical waveguide excited at or close to its resonance frequency.

5. The apparatus of claim 1, wherein the 2-D optical projector is a parallel projector that is a 2-D optical array configured to project a pattern that is a 2-D closed curve.

6. The apparatus of claim 1, wherein the reflective scanner is configured to perform slow beam scanning at speeds slower than 60 Hz.

7. The apparatus of claim 6, wherein the scanner is a rotary scanner configured to perform slow beam scanning.

8. The apparatus of claim 6, wherein the scanner is configured to perform slow beam scanning over a limited range of angular deviations.

9. The apparatus of claim 1, wherein the 2-D closed curve is an ellipse of which the length of the major axis is less than 120% of the minor axis.

10. The apparatus of claim 1, wherein a combination of the 2-D optical projector and the reflective scanner generate a cycloid trajectory.

11. The apparatus of claim 1, wherein the distal section has a longitudinal axis, and wherein the focusing optics has low numerical aperture and has an optical axis aligned on the longitudinal axis.

12. The apparatus of claim 1, wherein the distal section has a characteristic radius, and wherein the focusing optics comprises plural focusing optics elements, and at least one focusing optics element is high numerical aperture with focal distance smaller than the characteristic radius of a rigid enclosure.

13. The apparatus of claim 1, wherein the set of focusing optics has a focusing optics element with focal position relative to the distal section that is adjustable.

14. The apparatus of claim 13, wherein the set of focusing optics comprises variable focus optics to adjust the focal position of the focusing optics element.

15. The apparatus of claim 13, wherein the distal section comprises section portions mated by a screw thread mechanism, and the 2-D projector and at least a portion of the focusing optics are on separate mated section portions whose separation distance can be adjusted by means of the threaded screw, which adjusts the focal position of the portion of the focusing optics.

16. The apparatus of claim 13, wherein the reflective scanner is configured to be adjusted in centration, tilt, or other position by a mechanical adjustment from outside of the distal section.

17. The apparatus of claim 13, wherein the distal section comprises a linear actuator to adjust the focal position of the focusing optics.

18. The apparatus of claim 17, wherein the linear actuator translates at least a portion of the focusing optics to adjust the focal position of the focusing optics.

19. The apparatus of claim 17, wherein the linear actuator translates the 2-D optical projector to adjust the focal position of the focusing optics.

20. The apparatus of claim 13, wherein the focal position of the focusing optics is determined by an angular position of the reflective scanner.

21. The apparatus of claim 13, wherein the focal position of the focusing optics is determined by the location of the sample being imaged relative to the distal section.

22. The apparatus of claim 1, wherein a light source provides plural wavelengths and at least one of the wavelengths is chosen for laser-induced marking or ablation.

23. The apparatus of claim 1, wherein the outer housing of the distal section has one or both of its ends shaped with a conical taper.

24. The apparatus of claim 1, wherein the outer housing of the distal section is constructed of at least two materials, wherein at least one material is optically transparent, and at least one material is optimized for a functional property other than optical transparency.

25. The apparatus of claim 1, wherein a central portion of the distal section has a diameter larger or smaller than the diameter of either end of the distal section.

26. The apparatus of claim 1, wherein the distal section includes at least one static fiducial landmark.

27. A method for optical imaging of a luminal organ or surgical cavity which comprises:
providing an apparatus of claim 1;
causing the apparatus to scan an optical beam over a luminal organ or surgical cavity;
acquiring the optical image of the luminal organ or surgical cavity; and
processing and reconstructing the optical image according to the optical trajectory.

28. The method of claim 27, wherein the distal section is actuated by pulling or pushing the tether over a length that exceeds the width of the 2-D closed curve pattern to cover a large field of view.

29. The method of claim 27, wherein the reflective scanner is controlled asynchronously with at least one other scanner in the distal section.

30. The method of claim 27, wherein the 2-D projector is made to cease actuation and the reflective scanner positions the optical beam over a region of interest for laser-induced ablation as indicated by the optical image.

31. The method of claim 27, wherein a portion of the 2-D closed curve optical pattern is used to reconstruct the optical image.

32. The method of claim 27, wherein multiple portions of the 2-D closed curve optical pattern are used to separately reconstruct multiple optical images.

33. The method of claim 32, wherein the separately reconstructed multiple optical images are further processed and then recombined to form a single optical image.

34. The method of claim 32, wherein the multiple optical images are acquired with different imaging modalities or imaging contrast by switching or modulating the light source wavelength, intensity or other parameter.

35. The method of claim 27, wherein focal position of the focusing optics is controlled synchronously with position of the scanner.

36. The method of claim 27, wherein focal position of the focusing optics is controlled synchronously with the location of the sample being imaged.

37. The method of claim 27, wherein the distal section includes at least one static fiducial landmark, the method further comprising:
obtaining reconstruction parameters based on location of the static landmark in an acquired optical image.

38. The method of claim 27 wherein the optical beam is projected in the 2-D closed curve multiple times between discrete steps of scan by the reflective scanner.

39. The method of claim 27 wherein an image is reconstructed by mapping data points to Cartesian locations.

40. The method of claim 27 wherein the reflective scanner is rotated in alternate directions.

41. The apparatus of claim 1 wherein the 2-D optical projector comprises multiple projector elements operating in parallel.

42. The apparatus of claim 1 wherein the reflective scanner scans the projected optical beam over a length at an outer surface of the transparent portion of the distal section that is at least ten times a major dimension of the 2-D closed curve.

43. The apparatus of claim 1 wherein the 2-D optical projector scans at a frequency that is 1000-10,000 times higher than the scan frequency of the reflective scanner.

44. The apparatus of claim 1 wherein the proximal sector has a light source and the tether comprises an optical waveguide that connects the light source to the 2-D optical projector.

45. The apparatus of claim 44 wherein the optical waveguide comprises multiple waveguide elements.

46. An apparatus of claim 44 wherein the 2-D optical projector comprises part of the optical waveguide.

* * * * *